(12) United States Patent
Schneider et al.

(10) Patent No.: US 10,335,581 B2
(45) Date of Patent: Jul. 2, 2019

(54) MEDICAL BALLOON INCLUDING PLEATS

(71) Applicant: Covidien LP, Mansfield, MA (US)

(72) Inventors: Mark Schneider, Mound, MN (US); Bradley Steele, Plymouth, MN (US); Christopher Anderson, Plymouth, MN (US); Kumin Yang, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 563 days.

(21) Appl. No.: 14/741,521

(22) Filed: Jun. 17, 2015

(65) Prior Publication Data

US 2015/0360008 A1    Dec. 17, 2015

Related U.S. Application Data

(60) Provisional application No. 62/013,219, filed on Jun. 17, 2014, provisional application No. 62/137,897, filed on Mar. 25, 2015.

(51) Int. Cl.
| | | |
|---|---|---|
| *A61M 25/10* | (2013.01) | |
| *A61B 17/22* | (2006.01) | |
| *B29C 48/09* | (2019.01) | |
| *B29C 48/00* | (2019.01) | |
| *B29L 31/00* | (2006.01) | |

(52) U.S. Cl.
CPC ......... *A61M 25/1002* (2013.01); *A61B 17/22* (2013.01); *A61M 25/10* (2013.01); *A61M 25/104* (2013.01); *A61M 25/1027* (2013.01); *A61M 25/1029* (2013.01); *B29C 48/0017* (2019.02); *B29C 48/0018* (2019.02); *B29C 48/09* (2019.02); *A61B 2017/22001* (2013.01); *A61B 2017/22051* (2013.01); *A61B 2017/22061* (2013.01); *A61M 25/1038* (2013.01); *A61M 2025/1004* (2013.01); *A61M 2025/109* (2013.01); *A61M 2025/1031* (2013.01); *A61M 2025/1086* (2013.01); *B29L 2031/7543* (2013.01)

(58) Field of Classification Search
CPC ...... A61M 25/1038; A61M 2025/1086; A61M 2025/1004
See application file for complete search history.

(56) References Cited

U.S. PATENT DOCUMENTS

| | | | | |
|---|---|---|---|---|
| 4,941,877 | A | * | 7/1990 | Montano, Jr. ..... A61M 25/1002 604/103.07 |
| 5,041,125 | A | * | 8/1991 | Montano, Jr. ..... A61M 25/1002 604/103.14 |
| 5,318,587 | A | | 6/1994 | Davey |
| 5,456,666 | A | | 10/1995 | Campbell et al. |

(Continued)

FOREIGN PATENT DOCUMENTS

| | | |
|---|---|---|
| WO | 9925417 A1 | 5/1999 |
| WO | 2008027088 A2 | 3/2008 |

OTHER PUBLICATIONS

International Search Report and Written Opinion for PCT/US2015/036168, dated Oct. 7, 2015, 16 pages.

(Continued)

*Primary Examiner* — Jenna Zhang

(57) ABSTRACT

A balloon for a balloon catheter includes a body section and cone sections. At least one of the cone sections defines a plurality of grooves spaced around the circumference of the cone section.

12 Claims, 32 Drawing Sheets

(56) References Cited

U.S. PATENT DOCUMENTS

| | | | |
|---|---|---|---|
| 5,458,572 A | | 10/1995 | Campbell et al. |
| 5,826,588 A | | 10/1998 | Forman |
| 6,013,055 A | * | 1/2000 | Bampos ............ A61M 25/1002 |
| | | | 604/103.07 |
| 6,652,485 B1 | | 11/2003 | Gaudoin et al. |
| 7,306,616 B2 | | 12/2007 | Eidenschink et al. |
| 2004/0225318 A1 | * | 11/2004 | Eidenschink ..... A61M 25/1038 |
| | | | 606/194 |
| 2006/0182873 A1 | * | 8/2006 | Klisch .............. A61B 17/32072 |
| | | | 427/2.1 |
| 2006/0276820 A1 | * | 12/2006 | Yamaguchi ........... A61M 25/10 |
| | | | 606/194 |
| 2007/0016278 A1 | | 1/2007 | Shippy, III et al. |
| 2008/0114294 A1 | * | 5/2008 | Holman ............ A61M 25/1002 |
| | | | 604/96.01 |
| 2008/0132836 A1 | | 6/2008 | Burton et al. |
| 2009/0204082 A1 | * | 8/2009 | Wesselmann ......... A61M 25/10 |
| | | | 604/264 |

OTHER PUBLICATIONS

Communication pursuant to Article 94(3) EPC for European Application No. 14 734 777.3, dated Nov. 28, 2017, 6 pages.
Extended European Search Report, Application No. 14 734 777.3, dated Nov. 30, 2017, 9 pages.

* cited by examiner

MEDICAL BALLOON INCLUDING PLEATS

CROSS-REFERENCE TO RELATED APPLICATIONS

The present application claims the benefit of U.S. Provisional Application Nos. 62/013,219, filed Jun. 17, 2014, and 62/137,897, filed Mar. 25, 2015, the entirety of each of which is incorporated by reference.

FIELD OF THE DISCLOSURE

The present disclosure generally relates to a medical balloon including grooves on at least a cone section of the balloon, and a method of forming the same.

BACKGROUND OF THE DISCLOSURE

Balloons mounted on the distal ends of catheters are widely used in medical treatment. The balloon may be used to widen a vessel into which the catheter is inserted, open a blocked vessel and/or deliver a medical device to a body location among other uses. The medical balloon includes a central body section, which is typically tubular, opposite cone sections at opposite longitudinal ends of the body section, and opposite waist sections at opposite longitudinal ends of the balloon. In use, the uninflated balloon is delivered to a treatment location within a body lumen (e.g., a blood vessel) by tracking through an introducer sheath and exiting a distal end of the sheath to reach the treatment location. Once the uninflated balloon has reached the treatment location, fluid is delivered into the balloon, thereby expanding the outer circumference of the balloon (i.e., balloon is inflated). After treatment, the balloon is deflated and "pulled back" into the introducer sheath. The balloon catheter can then be withdrawn from the introducer sheath and the patient's body. It may be necessary or desired to re-introduce the balloon catheter into a body lumen, through the introducer sheath, to further treat the body lumen.

One known method of forming a medical balloon involves blow molding. In particular, the balloon is formed by radially expanding a segment of extruded polymer tubing, called a parison, in a mold. Balloons produced by radially expanding a parison typically have thicker waist sections and cone sections than the thickness of their body sections. The thicker cone sections may interfere with refolding of the balloon upon deflation (i.e., after treatment), which can make it difficult to pull the balloon back into the introducer sheath. This interference with re-folding may also make it difficult for the user to re-introduce the deflated balloon into the sheath after withdrawing the balloon catheter from the patient's body.

SUMMARY OF THE DISCLOSURE

In one example, a balloon for a balloon catheter includes a body section and cone sections. At least one of the cone sections defines a plurality of grooves spaced apart around a circumference of the cone section. The width of the groove may taper toward the body section. At least one of distal and proximal end sections of a bottom portion of each groove may be generally flat and extend at an angle offset with respect to a circumferential plane defined by the circumference of the corresponding proximal and distal cone sections. The grooves facilitate folding of the balloon to reduce at least a pull-back force of the balloon. The balloon may be blow molded. The balloon may have other features without departing from the scope of the present invention.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
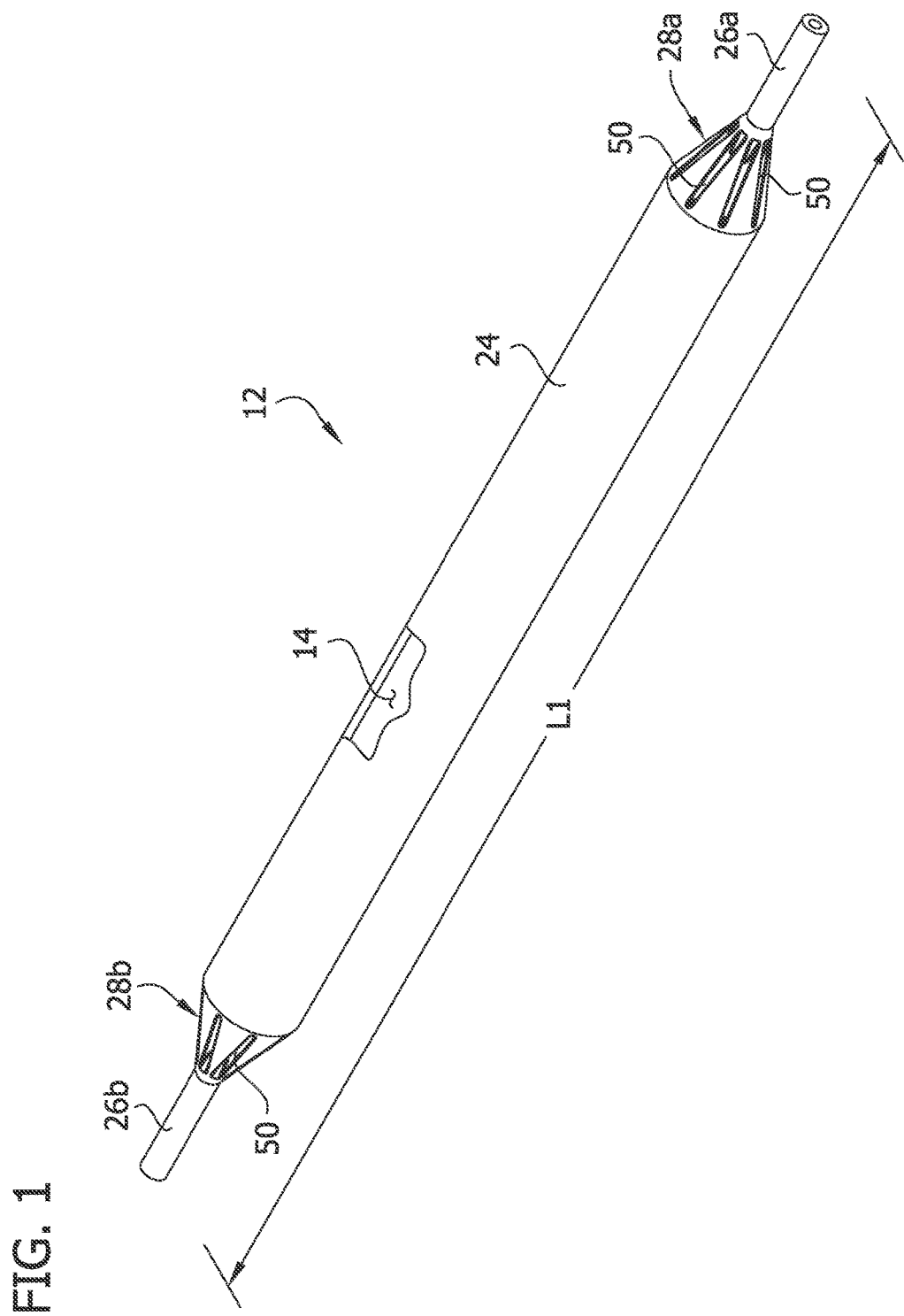
FIG. 1 is a perspective of one embodiment of a medical balloon for a balloon catheter.

Referring to FIG. 1, one embodiment of a medical balloon for a medical device is generally indicated at reference numeral 12 in FIG. 1. The balloon defines an interior chamber 14 for receiving fluid therein to expand an outer circumference (i.e., an outer periphery) of the balloon. The balloon 12 is shown in its expanded or inflated configuration throughout the drawings, with the understanding that in its uninflated and deflated configurations, the balloon is capable of folding lengthwise such that the outer circumference of the balloon in its uninflated and deflated configurations is substantially less than the outer circumference of the balloon in its expanded configuration. With respect to any or all of the below described embodiments of the present disclosure, the medical balloon 12 may be secured to a catheter, generally indicated at 16 in FIG. 2, such that a catheter body 18 of the catheter extends axially through the interior chamber 14 of the balloon, as is generally known in the art, to form a balloon catheter, generally indicated at 20. The balloon 12 and catheter body 18 have suitable shapes and dimensions for introduction into a desired body lumen for treatment therein. Typically, the balloon 12, in its uninflated initial configuration, is introduced into the body lumen using an introducer sheath (not shown). The uninflated balloon 12 is delivered to a treatment location within a body lumen (e.g., a blood vessel) by tracking through the introducer sheath and ultimately exiting a distal end of the sheath to reach the treatment location. Once the uninflated balloon 12 has reached the treatment location, fluid is delivered into the balloon, thereby expanding the outer circumference of the balloon (i.e., balloon is inflated). After treatment, the balloon 12 is deflated and "pulled back" into the introducer sheath. The balloon catheter 20 can then be withdrawn from the introducer sheath and the patient's body. It may be necessary or desired to re-introduce the balloon catheter 20 into a body lumen, through the introducer sheath, to further treat the body lumen.

The illustrated balloon catheter 20 may be configured for introduction along and inflation (i.e., circumferential or peripheral expansion) within a blood vessel for treating vascular stenosis. As an example, the medical balloon 12 of the illustrated balloon catheter 20 may be configured for introduction along and inflation within one or more of peripheral arteries and veins, coronary arteries and veins, renal arteries and veins, cerebral arteries and veins, and carotid artery. In other examples, the medical balloon 12 may be configured for introduction along and inflation within other body lumens for treating stenosis of those lumens. The balloon 12 may be configured for treating other body lumens and/or for other treatments of those lumens.

Referring to FIG. 1, the medical balloon 12 has a length L1 and comprises a balloon body section 24; opposite proximal and distal waist sections 26a, 26b, respectively, at opposite longitudinal ends of the balloon; and opposite proximal and distal cone sections, generally indicated at 28a, 28b, respectively, at corresponding proximal and distal ends of the body section intermediate the body section and the corresponding proximal and distal waist sections. As explained in more detail below, the body section 24, waist sections 26a, 26b, and cone sections 28a, 28b may be integrally formed during a blow molding process to form the balloon 12 as a one-piece construction. It is understood that the balloon 12 may have other sections, structures, and/or components without departing from the scope of the present invention.

The balloon 12 may be formed from a polymer material, including, but not limited to, a thermoplastic polymer or a thermoplastic elastomer polymer. For example, suitable materials for the balloon include polyesters such as PET, PEN and PBT; polyurethane block copolymers such as ISOPLAST 301, PELLETHANE 2363-75D; polyamide block copolymers such as PEBAX 6333, PEBAX 7033 and PEBAX 7233; polyamides such as nylon 12, nylon 11, and nylon 10; polymer blend materials such as single or multi-phase blends of liquid crystal polymers in another polymer; and polyester elastomer balloons such as ARNITEL EM 740 and HYTREL 8238. Other materials do not depart from the scope of the present invention as defined by the claims. In one example, the balloon 12 may be free from a lubricious coating (hydrophobic or hydrophilic), although in other examples the balloon may include such a lubricious coating.

Figure 3:
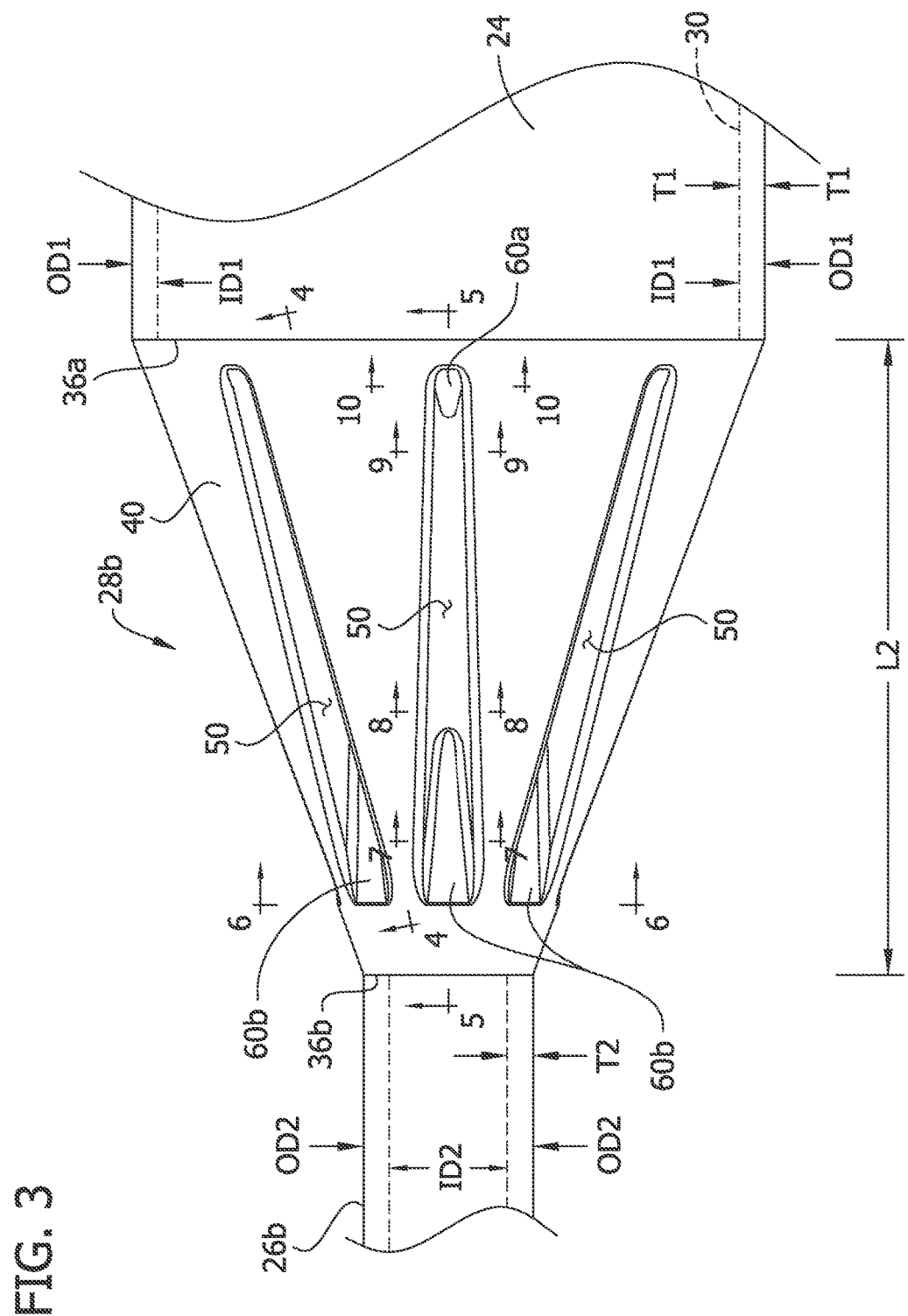
FIG. 3 is an enlarged, fragmentary side elevational view of the balloon of FIG. 1, showing a distal cone section, a portion of a distal waist section, and a portion of the body section thereof.

As shown in FIG. 1, the body section 24 interconnects and is disposed between the distal and proximal cone sections 28a, 28b. In the illustrated embodiment, the body section 24 is generally tubular defining a portion of the interior chamber 14 for receiving fluid to expand an outer circumference (i.e., an outer dimension) of the body section. Referring to FIG. 3, the body section 24 has an expanded inner diameter ID1 (i.e., an inner cross-sectional dimension) defined by an interior surface 30 of the balloon 12, an expanded outer diameter OD1, and a thickness T1 that may be generally uniform along its length L1. In one example, the expanded outer diameter OD1 may measure greater than about 3 mm, and in one example, from about 3 mm to about 30 mm, the single-wall thickness T1 may measure from about 0.0005 in (0.0127 mm) to about 0.003 in (0.0762 mm), and the length L1 of the balloon may measure about 10 mm to about 250 mm. The body section 24 may have other shapes and dimensions without departing from the scope of the present invention.

The distal and proximal waist sections 26a, 26b are generally tubular and, in the illustrated embodiment, are configured to receive the catheter body 18 therein. Referring to FIG. 3, each waist section 26a, 26b has an outer diameter OD2 less than the outer diameter OD1 of the body section 24. Thicknesses T2 of the waist sections 26a, 26b may be greater than the thickness T1 of the body section 24. It is understood that the waist sections 26a, 26b may be omitted from the balloon 12 without departing from the scope of the present invention.

Figure 4:
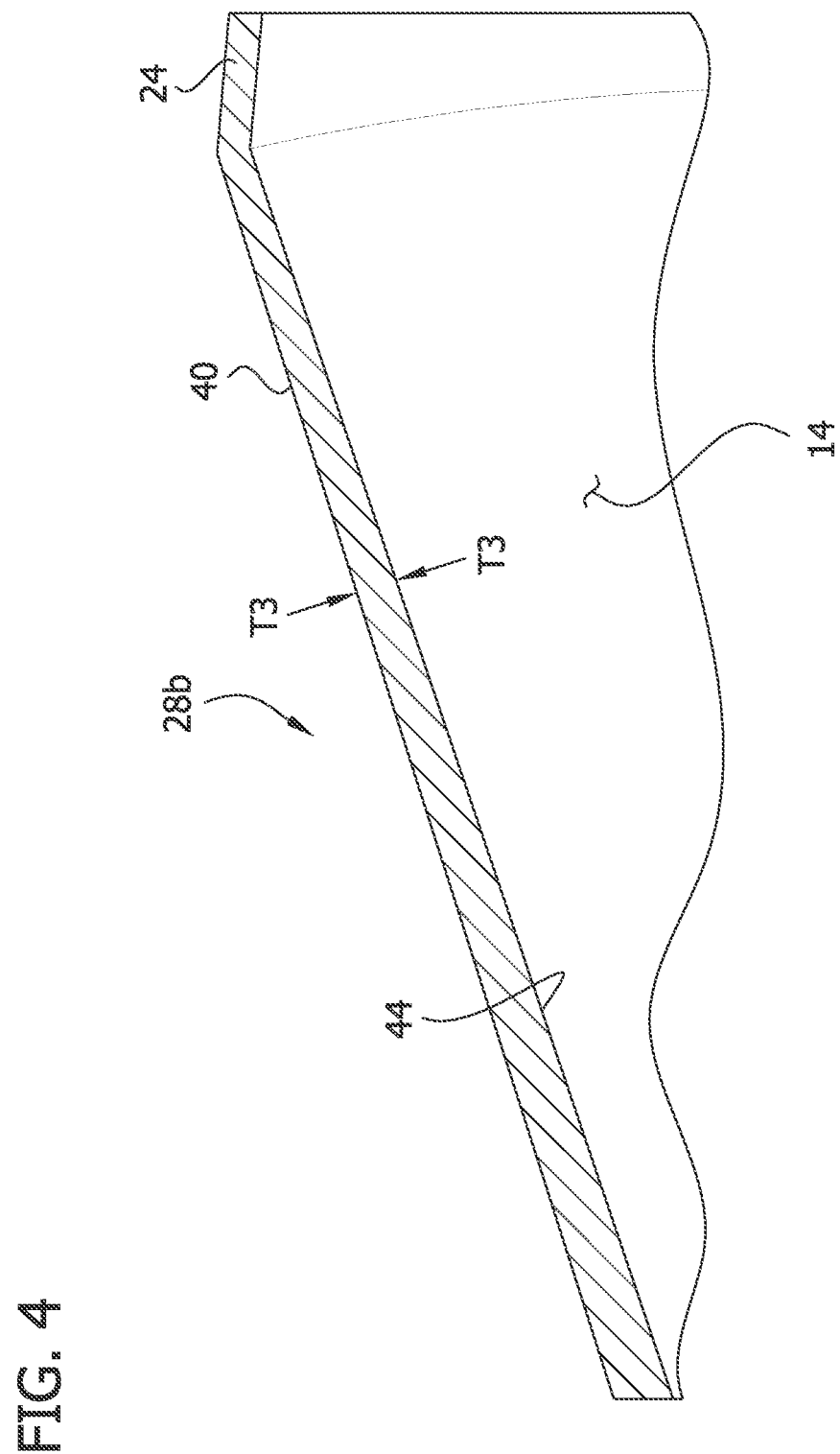
FIG. 4 is an enlarged, fragmentary section of the balloon taken along the line 4-4 in FIG. 3.

In general, the distal and proximal cone sections 28ab, 28b are mirror images of one another. For purposes of this disclosure, the proximal cone section 28b is shown in detail in the drawings, with the understanding that the teachings relating to the proximal cone section apply equally to the distal cone section 28a, with exceptions noted herein. Referring to FIG. 3, the proximal cone section 28b has distal and proximal ends 36a, 36b, a length L2 extending between the distal and proximal ends, and an exterior surface 40 having a generally conical (e.g., frustoconical) shape and a circumference or periphery (i.e., an outer dimension) and an outer diameter (i.e., an outer cross-sectional dimension) tapering proximally toward the proximal end of the proximal cone section. An interior surface 44 of the proximal cone section 28b also has a generally conical shape defining an inner circumference or periphery (i.e., an inner dimension) and an inner diameter (i.e., an inner cross-sectional dimension) of the cone section that taper proximally toward its proximal end 36b. As shown in FIG. 4, a wall thickness T3 of the proximal cone section 28b between the interior and exterior surfaces 40, 44 generally increases toward the proximal end 36b thereof and the proximal waist section 26b, such that the proximal cone section has a maximum wall thickness generally adjacent to the proximal waist section. Described another way, the wall thickness T3 of the proximal cone section 28b tapers toward the distal end 36a thereof and the body section 24.

In the illustrated embodiment, the structures of the distal cone section 28a have inverse relationships with the corresponding structures of the proximal cone section 28b. Although not shown in detail in the drawings, the distal cone section 28a has proximal and distal ends, a length extending between the proximal and distal ends, and an exterior surface having a generally conical shape and defining an outer circumference or periphery (i.e., an outer dimension) and an outer diameter (i.e., an outer cross-sectional dimension) of the cone section that taper distally toward its proximal end. An interior surface of the distal cone section also has a generally conical shape and defines an inner circumference or periphery (i.e., an inner dimension) and an inner diameter (i.e., an inner cross-sectional dimension) of the cone section that taper distally toward the distal end thereof. A thickness of the distal cone section between the interior and exterior surfaces generally increases toward the distal end thereof and the distal waist section, such that the distal cone section has a maximum wall thickness generally adjacent to the distal waist section. Described another way, the thickness of the distal cone section tapers toward the proximal end thereof and the body section.

Figure 2:
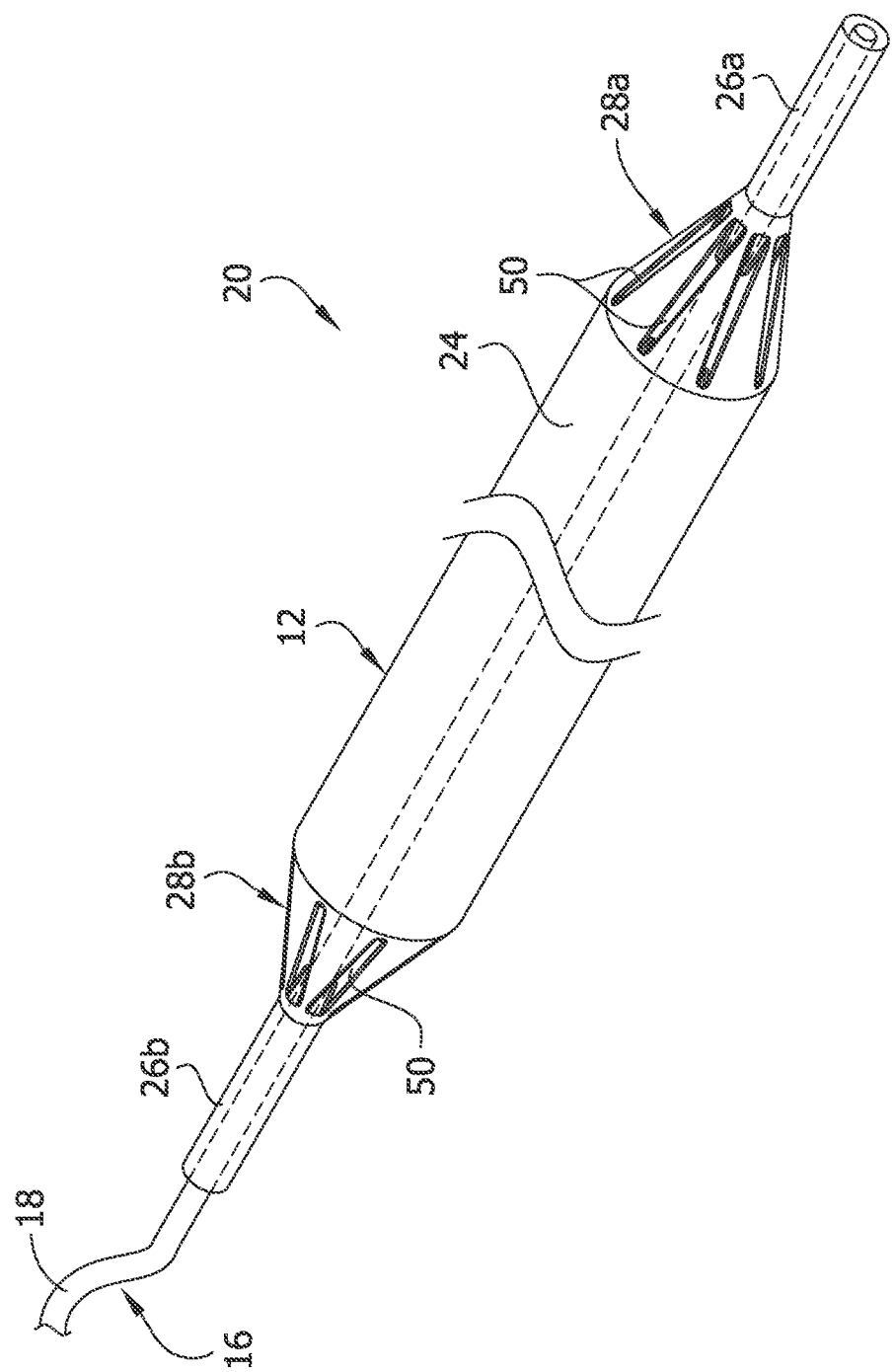
FIG. 2 is a fragmentary perspective of a balloon catheter including the balloon of FIG. 1.
Figure 6:
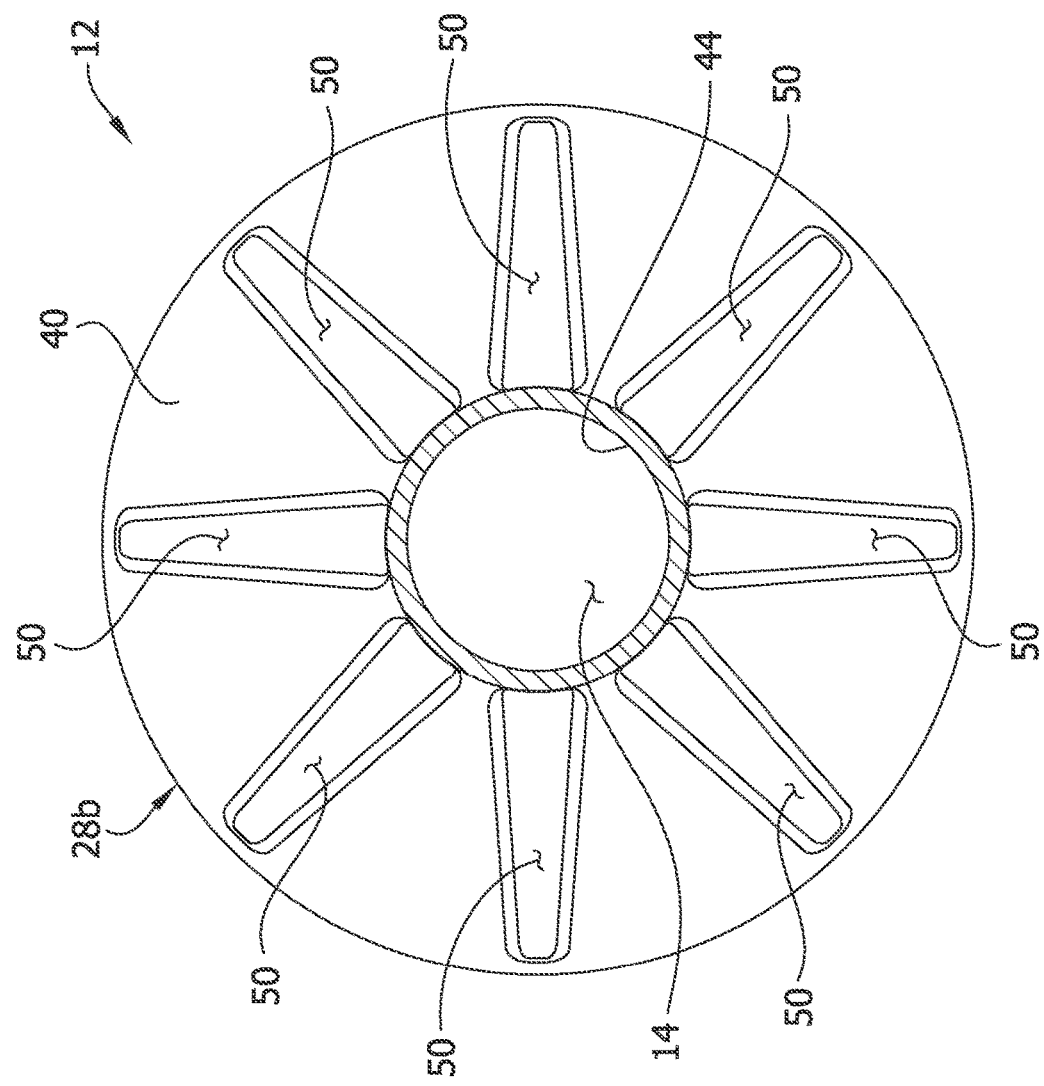
FIG. 6 is an enlarged section of the balloon taken along the line 6-6 in FIG. 3.

Referring to FIGS. 1 and 2, at least one of the cone sections 28a, 28b comprises grooves 50 to facilitate folding of the balloon 12. In the illustrated embodiment, each of the distal and proximal cone sections 28a, 28b defines such grooves 50, as shown in FIGS. 1 and 2. In other embodiments, only the distal cone section 28a or only the proximal cone section 28b may include the grooves 50. As seen in FIG. 6, the grooves 50 are spaced apart from one another around the outer circumference (i.e., outer periphery) of the corresponding cone section 28a, 28b, and in the illustrated embodiment, the grooves 50 are uniformly spaced apart from one another. One or both cone sections 28a, 28b may include any suitable number of grooves 50. In one example, the number of grooves 50 is based, at least in part, on the outer diameter OD1 (i.e., outer cross-sectional dimension) of the body portion 24 of the balloon 12. For example, one or both of the cone sections 28a, 28b includes one groove 50 for every millimeter in outer diameter OD1 of the body section 24. As an example, balloon including a body section having an outer diameter measuring 8 mm will have 8 grooves (or at least 8 grooves) on one or both of the cone sections. In one embodiment, the grooves 50 are formed during blow molding, as explained below. In other embodiments, the grooves 50 may be formed in other ways, such as by grinding or laser ablation.

Figure 5:
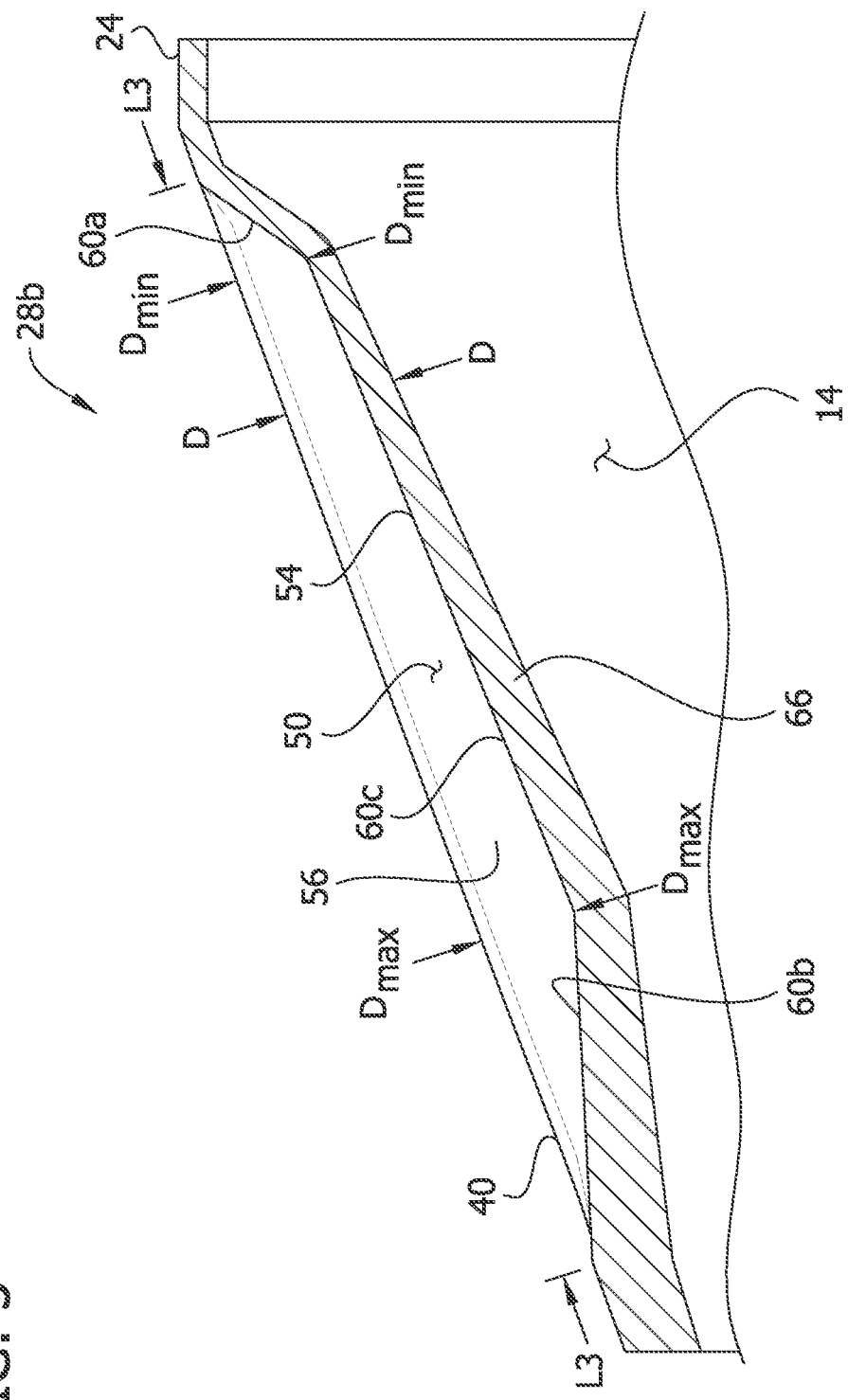
FIG. 5 is an enlarged, fragmentary section of the balloon taken along the line 5-5 in FIG. 3.

Referring to FIG. 5, a single groove 50 of the proximal cone section 28b is shown for illustrative purposes, with the understanding that the teachings of the illustrated groove apply equally to the other grooves of the cone section or sections. The groove 50 is defined by a bottom portion 54 and opposing side wall portions 56 extending from respective sides of the bottom portion to the exterior surface 40 of the proximal cone section 28b. The bottom portion 54 has opposite distal and proximal end sections 60a, 60b extending from corresponding proximal and distal ends of a central section 60c of the bottom portion to the exterior surface 40 of the proximal cone section 28b. In the illustrated embodiment, the distal and proximal end sections 60a, 60b of the bottom portion 54 are generally flat (see FIGS. 7 and 10), and the central longitudinal section 60c of the bottom portion is generally arcuate in cross section (see FIGS. 8 and 9). As shown in FIG. 5, the distal and proximal end sections 60a, 60b of the bottom portion 54 extend at angles offset from a circumferential plane defined by the circumference or periphery of the proximal cone section 28b. The distal and proximal end sections 60a, 60b also extend in diverging directions from the central section 60c to the exterior surface 40 of the proximal cone section 28b. As explained in more detail below, the flat distal and proximal end sections 60a, 60b and the arcuate central section 60c of the bottom portion 54 defining the groove 50 are formed by corresponding portions of a mold to facilitate releasing of the blow-molded balloon from the mold.

Referring still to FIG. 5, the groove 50 has a length L3 extending lengthwise of the proximal cone section 28b between the proximal and distal ends of the proximal cone section, and a depth D extending inward from the exterior surface 40 of the proximal cone section. In the illustrated embodiment, the depth D of at least a portion of the groove 50 (i.e., a central longitudinal portion that is partially defined by the central longitudinal section 60c of the bottom portion 54 defining the groove) tapers toward the body section 24. That is, the depth D of the groove 50 tapers distally toward the distal end thereof and the body section 24. This tapering depth D is also evident from FIGS. 8 and 9, where the depth (indicated at D1) of the groove 50 taken at line 8-8 in FIG. 3 is greater than the depth (indicated at D2) of the groove taken at line 9-9 in FIG. 3. Inversely, the depth of at least a portion of each groove 50 of the distal cone section 28a (i.e., the central longitudinal section 60c) tapers proximally toward the proximal end thereof and the body section 24. Through this configuration, as shown in FIG. 5, a maximum depth $D_{max}$ of each groove 50 is generally adjacent the respective waist sections 26b, 26c, where the cone sections 28a, 28b have maximum thicknesses, and a minimum depth $D_{min}$ of each groove is generally adjacent the body section 24. It is believed that the maximum depths $D_{max}$ of the grooves 50 at these locations facilitate folding and refolding of the balloon 12 at the locations generally adjacent the respective waist sections 26a, 26b, where the cone sections 28a, 28b have maximum thicknesses. Thus, the grooves 50 facilitate refolding of the balloon 12 after deflation to reduce the cross-sectional profile (e.g., the circumference) of the deflated balloon. Facilitating re-folding of the balloon 12 into a low cross-sectional profile decreases the pull-back force necessary to pull the balloon back into the introducer sheath after treatment. It is understood that in other embodiments, the depths D of the grooves may not taper lengthwise.

Figure 7:
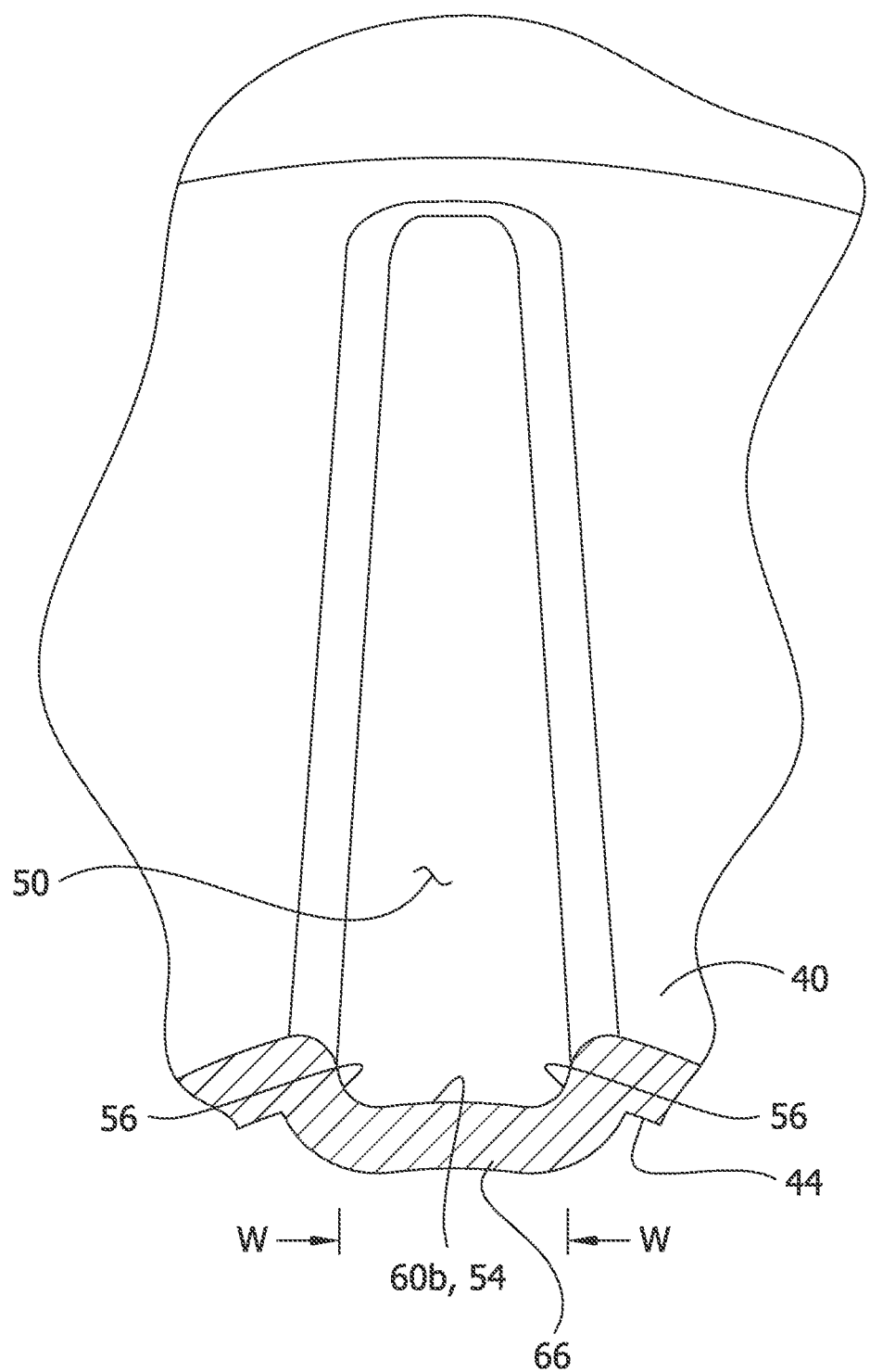
FIG. 7 is an enlarged, fragmentary section of the balloon taken along the line 7-7 in FIG. 3.

Referring to FIG. 7, the groove has a width W defined between the opposing side wall portions 56 and extending circumferentially of the corresponding cone section. The width W of at least a longitudinal portion of the groove 50 tapers toward the body section 24. That is, the width W of at least a portion of each groove 50 of the proximal cone section 28b tapers distally toward the distal end thereof and the body section 24, and the width of at least a portion of each groove of the distal cone section 28a tapers proximally toward the proximal end thereof and the body section. This tapering width W is also evident from FIGS. 8 and 9, where the width (indicated at W1) of the groove 50 taken at line 8-8 in FIG. 3 is greater than the width (indicated at W2) of the groove taken at line 9-9 in FIG. 3. Through this configuration, a maximum width of each groove 50 is generally adjacent the respective waist sections 26a, 26b. It is believed that the maximum widths of the grooves 50 at these locations facilitate folding of the balloon 12 at the locations generally adjacent the respective waist sections 26a, 26b, where the cone sections 28a, 28b have maximum thicknesses. Thus, the grooves 50 facilitate refolding of the balloon 12 after deflation to reduce the cross-sectional profile (e.g., the circumference) of the deflated balloon. Facilitating re-folding of the balloon 12 into a low cross-sectional profile decreases the pull-back force necessary to pull the balloon back into the introducer sheath after treatment. It is understood that in other embodiments, the widths W of the grooves may not taper lengthwise or the widths may taper away from the body section.

Figure 8:
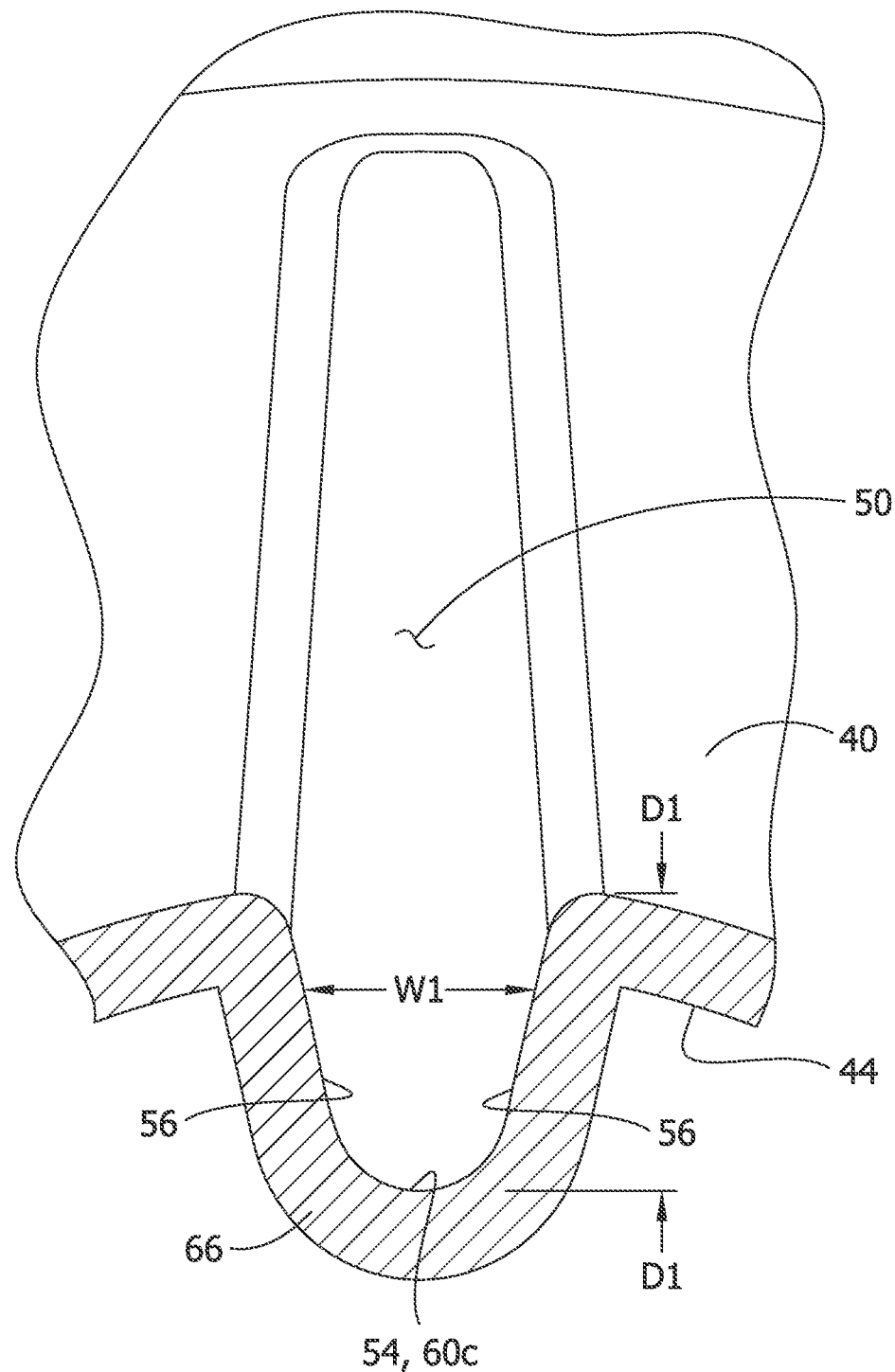
FIG. 8 is an enlarged, fragmentary section of the balloon taken along the line 8-8 in FIG. 3.
Figure 9:
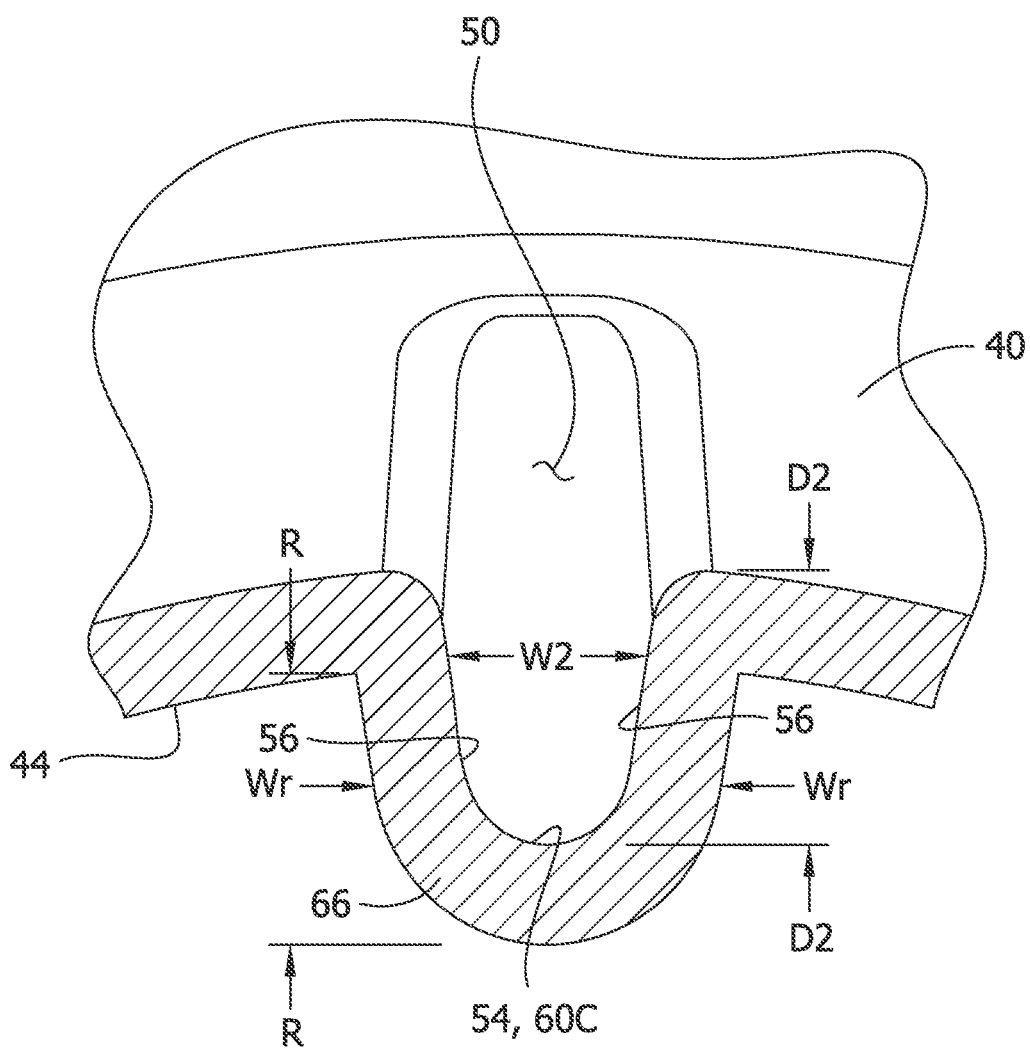
FIG. 9 is an enlarged, fragmentary section of the balloon taken along the line 9-9 in FIG. 3.
Figure 10:
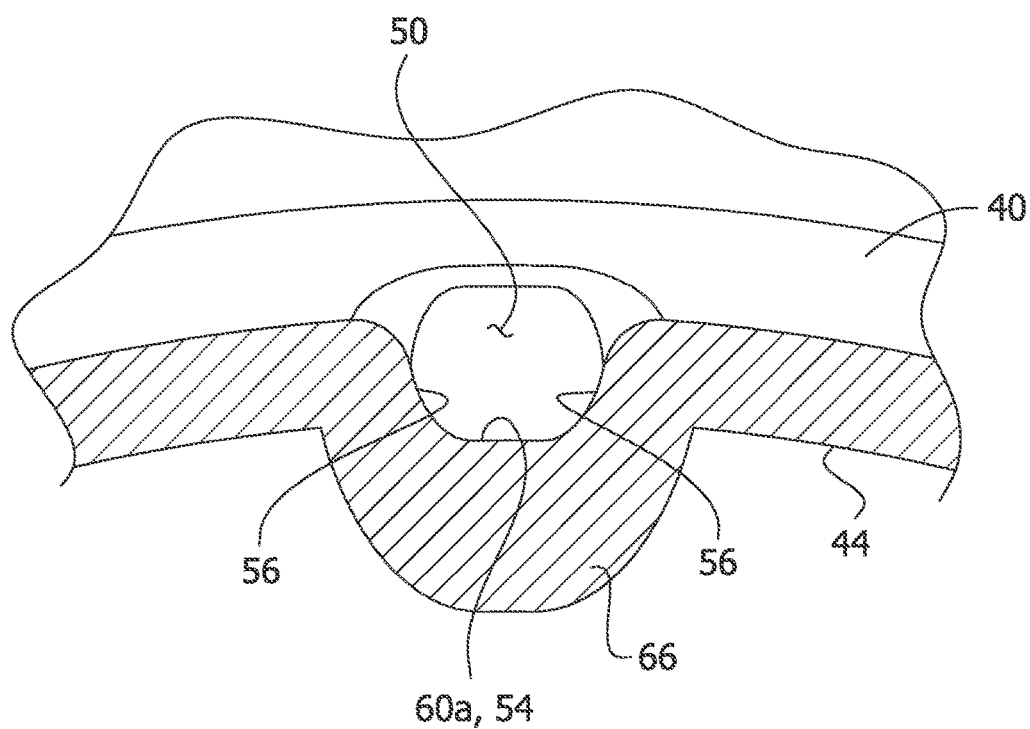
FIG. 10 is an enlarged, fragmentary section of the balloon taken along the line 10-10 in FIG. 3.

As can be seen from FIGS. 8 and 9, in particular, the width W of at least a portion of the groove 50 also tapers from adjacent the exterior surface 40 of the proximal cone section 28b toward the bottom portion 54 of the groove. This configuration facilitates releasing of the blow-molded balloon from the mold. It is understood that in other embodiments, the widths W of the grooves may not taper depthwise.

In the illustrated embodiment, the cone sections 28a, 28b have corresponding internal ribs 66 associated with the grooves 50 (e.g., each groove has an associated rib). In other words, each of the distal and proximal cone sections 28a, 28b includes ribs disposed at locations on the interior surface of the corresponding cone section generally corresponding to locations of the grooves on the exterior surface of the corresponding cone section. The internal ribs 66 extend inward from the interior surface 44 of the corresponding cone section 28a, 28b a radial distance R (see, e.g., FIG. 9). As explained in more detail below, the dimensions of the rib—including the lengths, widths, and radial distances R thereof—are based on the dimensions of mold ribs of the mold used to blow-mold the balloon and the thicknesses of the cone sections, which are based on the thickness of the parison and the dimensions (e.g., inner diameters) of the mold. In illustrated embodiment, the dimensions of each rib 66 are directly related to the dimensions of the corresponding groove 50. Thus, in the illustrated embodiment, the radial distance R of each rib 66 tapers toward the body section 24 and a width Wr of each rib (see, e.g., FIG. 9) tapers lengthwise toward the body section and radially away from the interior surface 44. It is believed that the internal ribs 66 facilitate folding of the balloon 12 at the locations generally adjacent the respective waist sections 26a, 26b, where the cone sections 28a, 28b have maximum thicknesses. Thus, the ribs 66 facilitate refolding of the balloon 12 after deflation to reduce the cross-sectional profile (e.g., the circumference) of the deflated balloon. Facilitating re-folding of the balloon 12 into a low cross-sectional profile decreases the pull-back force necessary to pull the balloon back into the introducer sheath after treatment. In other embodiments, the cone sections may not include the internal ribs. As can be understood, in such an embodiment, the thicknesses of the cone sections are greater than the heights of the groove-forming ribs of the mold.

Figure 11:
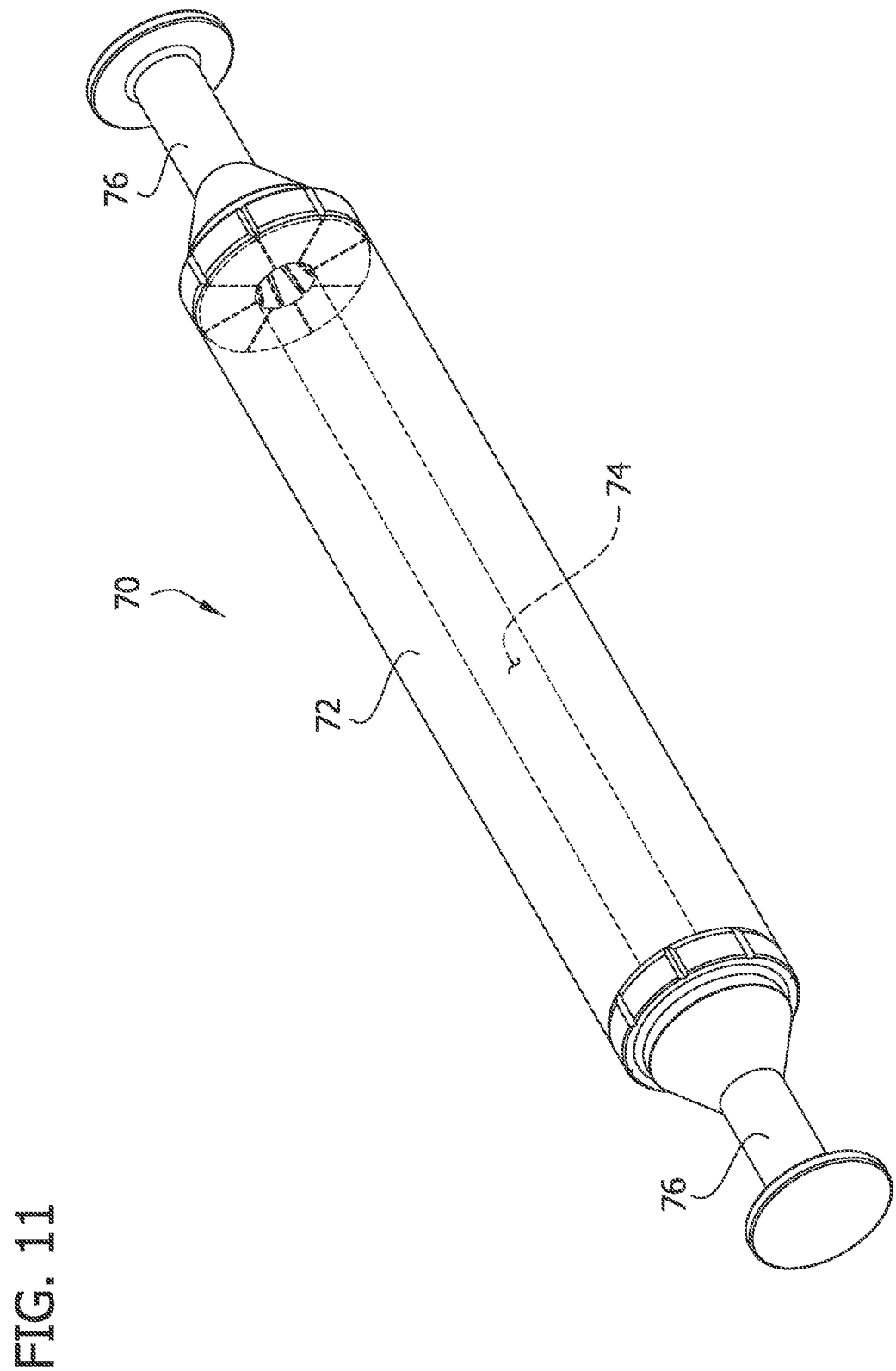
FIG. 11 is a schematic perspective of one embodiment of a blow mold for use in forming a balloon.

Referring to FIG. 11, one embodiment of a mold for use in blow molding the medical balloon is illustrated schematically at reference numeral 70. The mold 70 comprises a body molding section 72 defining a body molding cavity 74, and opposite proximal and distal cone-waist molding sections, generally indicated at 76, at respective proximal and distal ends of the body molding section and defining respective cone molding cavities 78 and waist molding cavities 79. The body molding cavity 74 is generally cylindrical having a circumference that defines an outer circumference (i.e., an outer dimension) of the body section 24 of the blow molded balloon 12. The cone molding cavity 78 of the cone-waist molding section 76 is used to form the corresponding proximal and distal balloon cones 28a, 28b during blow molding, and the waist molding cavities 76 are used to form the corresponding proximal and distal balloon waists 26a, 26b during blow molding.

Figure 12:
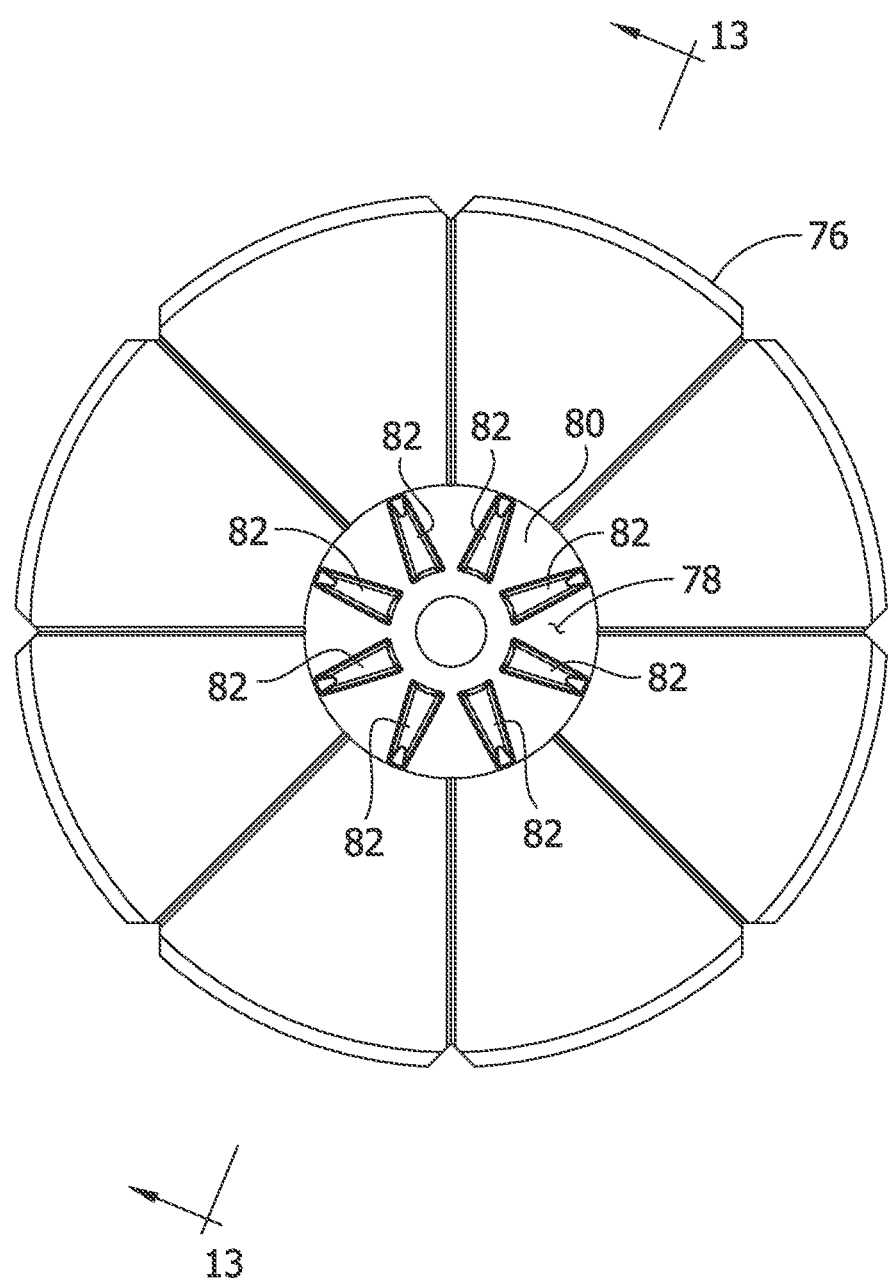
FIG. 12 is a front elevational view of cone-waist molding section of the blow mold.
Figure 13:
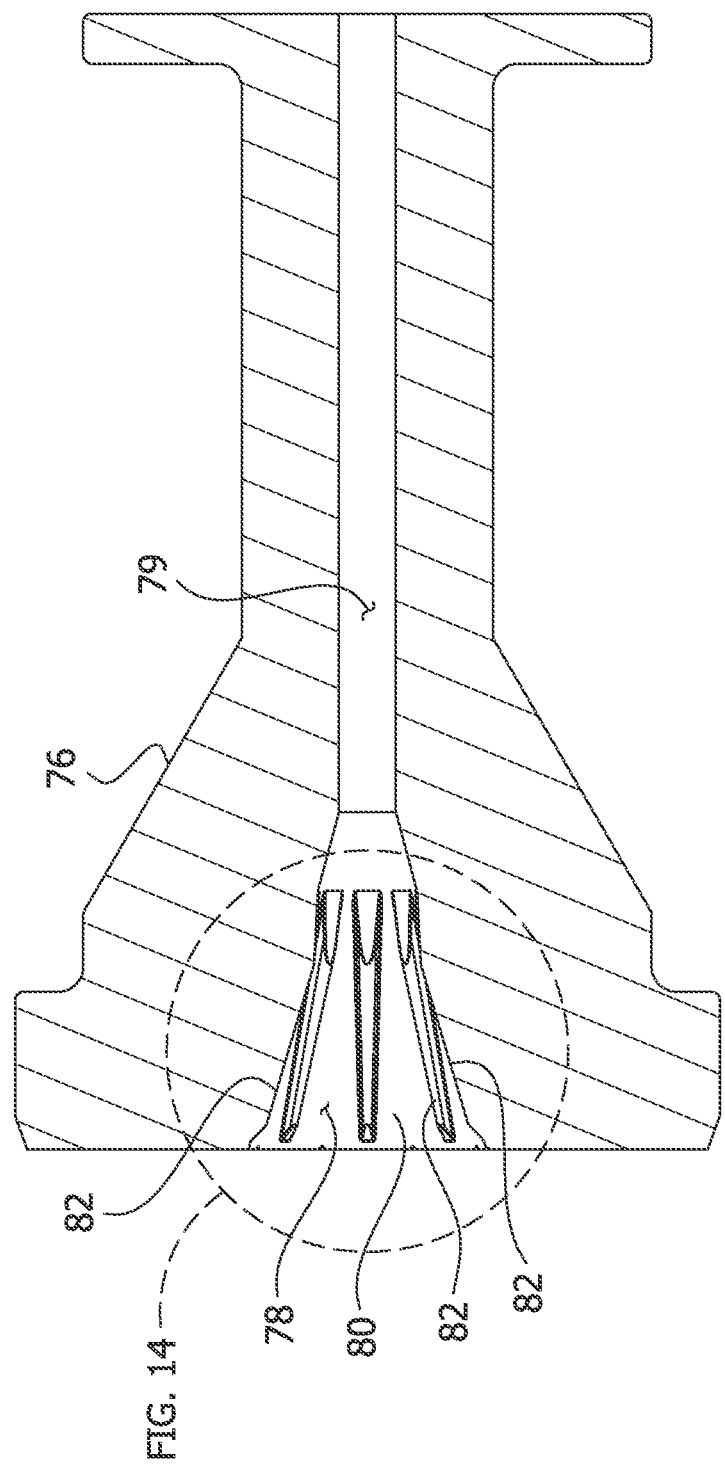
FIG. 13 is a longitudinal section of the cone-waist molding section.
Figure 14:
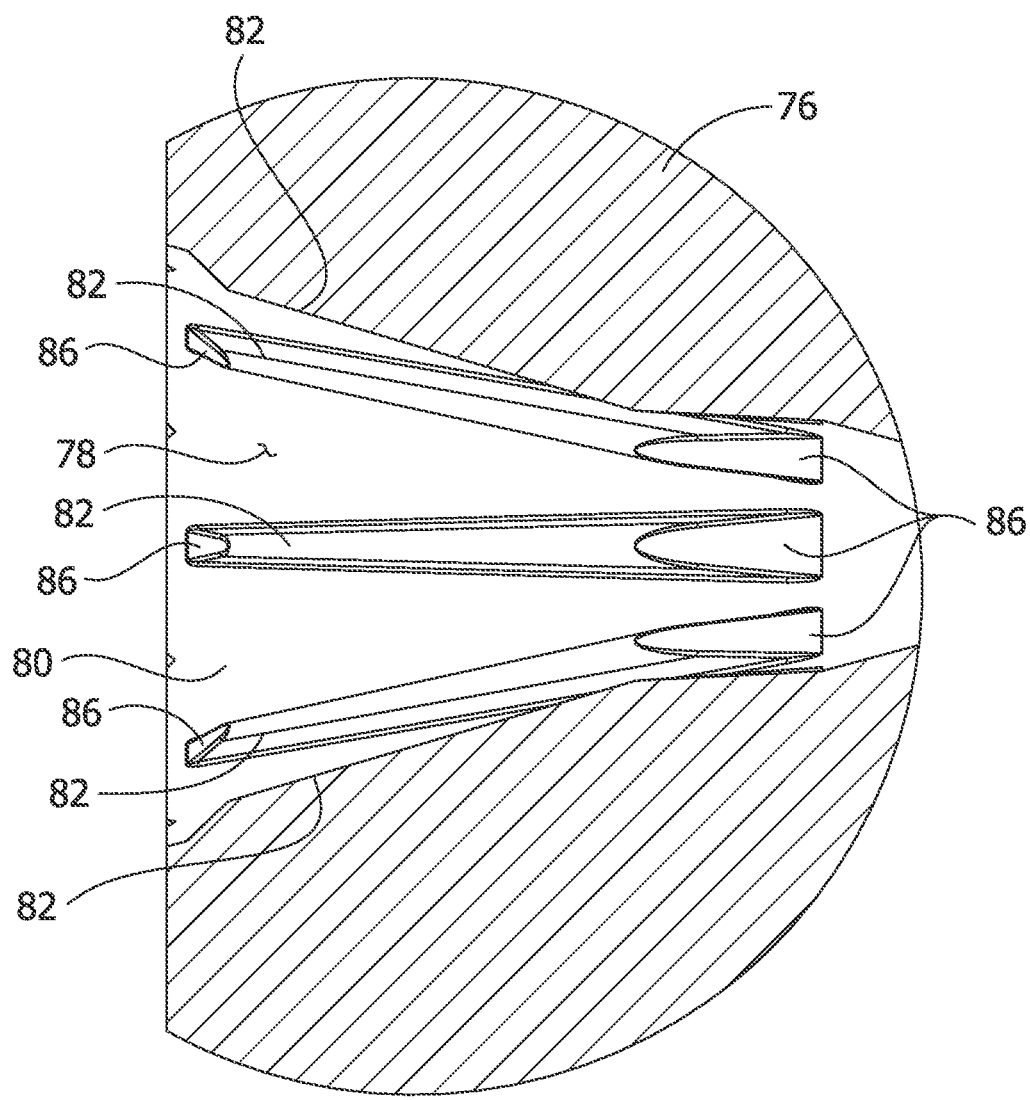
FIG. 14 is an enlarged, partial view of FIG. 13.

Referring to FIGS. 12 and 13, one of the cone-waist molding sections 76 will be described with the understanding that the other cone-waist molding section is identical, other than being positioned on an opposite end of the body molding section 72. The waist molding cavity 79 is defined by a generally cylindrical shaped interior surface 80 of the cone-waist molding section 76, although the interior surfaces defining the waist molding cavities may have shapes other than cylindrical without departing from the scope of the present invention. The cone molding cavity 78 is defined by a generally conical shaped interior surface 80 of the corresponding cone-waist molding section 76, and a plurality of molding ribs 82 extending radially inward from the interior surface. As can be understood, the shape and sizes of the respective interior surface 80 and molding ribs 82 of the illustrated cone-waist molding section 76 are suitable for forming the cone sections 28a, 28b of the illustrated balloon 12 during a blow molding process. For example, the conical interior surface 80 of the cone-waist molding section 76 has a size and shape corresponding to the size and shape of the exterior surfaces 40 of the cone sections 28a, 28b of the balloon 12. Moreover, the molding ribs 82 have sizes, shapes and locations corresponding to the sizes, shapes and locations of the grooves 50 of the cone sections 28a, 28b of the balloon. For example, each molding rib 82 has end portions 86 (see, e.g., FIG. 14) that are generally flat to facilitate releasing the balloon 12 from the mold. These end portions 86 form the bottom end sections 60a, 60b of the bottom portions 54 of the grooves 50.

One example of blow molding the balloon 12 using the mold will now be described. A parison or pre-form (not shown) is provided. The parison may comprise an extruded tube of polymeric material. In one example, the parison may have a uniform thickness along its length, although the thickness of the parison may vary along its length. The parison is inserted into the mold 70, heated to soften the polymer, and injected with a fluid (e.g., nitrogen gas) to pressurize the interior of the parison and expand the parison. Upon expansion of the heated parison, the parison takes on the shape of the mold to form the body section 24, the waist portions 26a, 26b, and the cone sections 28a, 28b, for example. The parison is then cooled in the mold to form the balloon 12. Additional steps may be carried out during this process, including but not limited to, a heat treating step and/or an axial stretching step.

The following non-limiting examples are provided to further illustrate embodiments of the present invention.

Test balloons having the illustrated grooves 50 and internal ribs 66 formed on the distal and proximal cone sections 28a, 28b were formed using a blow mold, similar to the illustrated blow mold 70. Control balloons were also formed using the same process as the test balloons with the grooves and ribs, except the grooves and ribs were omitted from the balloons. Other than the grooves and ribs, the two groups of balloon were identical in shape, size and polymer. The inflated diameters of the body sections of the test and control balloons measured 6 mm and the lengths of the test and control balloons measured 100 mm (i.e., 6×100 mm balloons). Each of the parisons or pre-forms used to form the balloons was extruded nylon 12 polymer.

Each of the balloons from the test and control groups was tested for the pull-back force required to pull the balloon, in its deflated configuration, back into a distal end of an introducer sheath. Each of the balloons from the test and control groups was also tested for the re-insertion force required to re-insert the deflated balloon into the introducer sheath. Each of these forces was determined using an apparatus suitable for measuring such forces. The overall results of the pull-back force test are shown in the chart provided in FIG. 15. FIG. 16 shows the results of the pull-back force with outliers removed. The overall results of the re-insertion force test are shown in the chart provided in FIG. 17.

Figure 15:
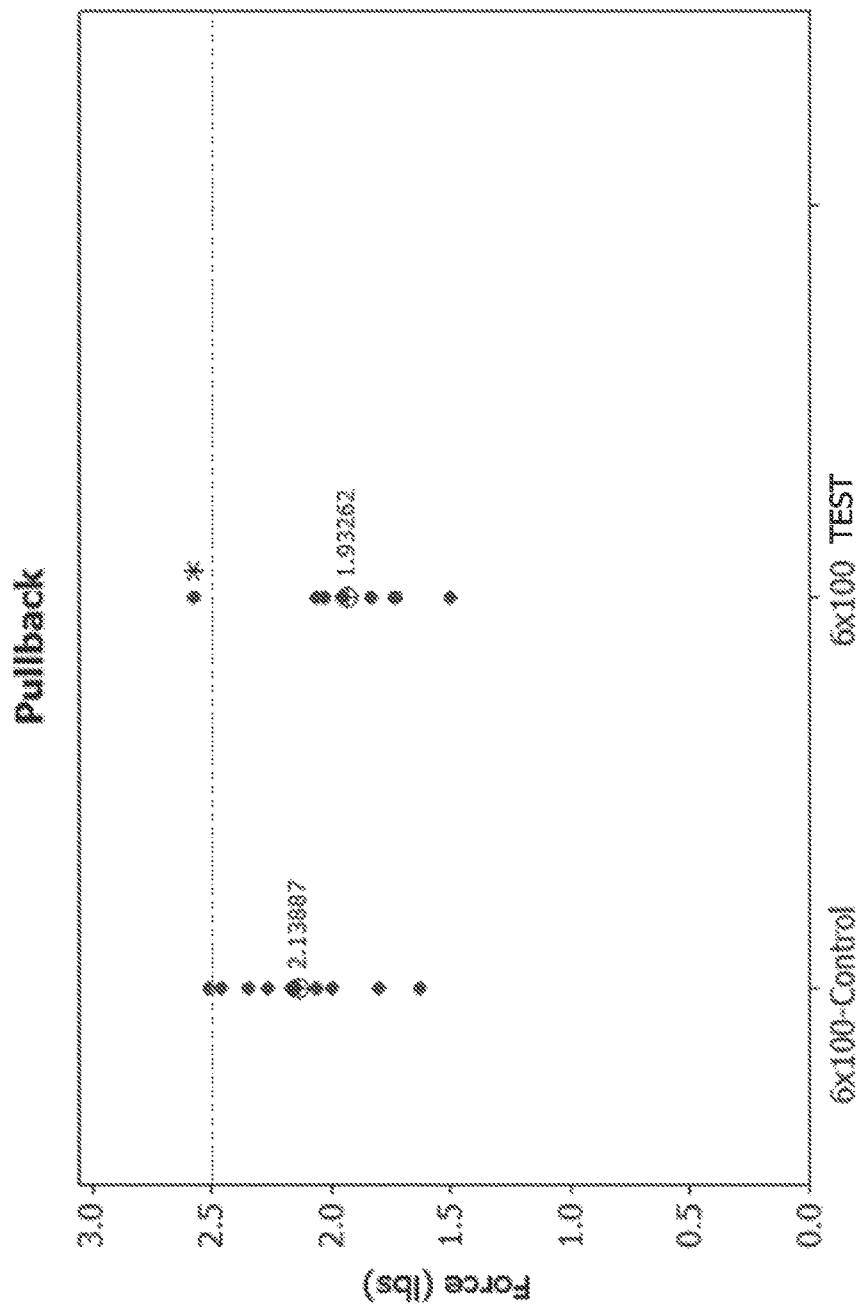
FIG. 15 is a chart depicting data collected during pull-back force testing of test balloons and control balloons.
Figure 16:
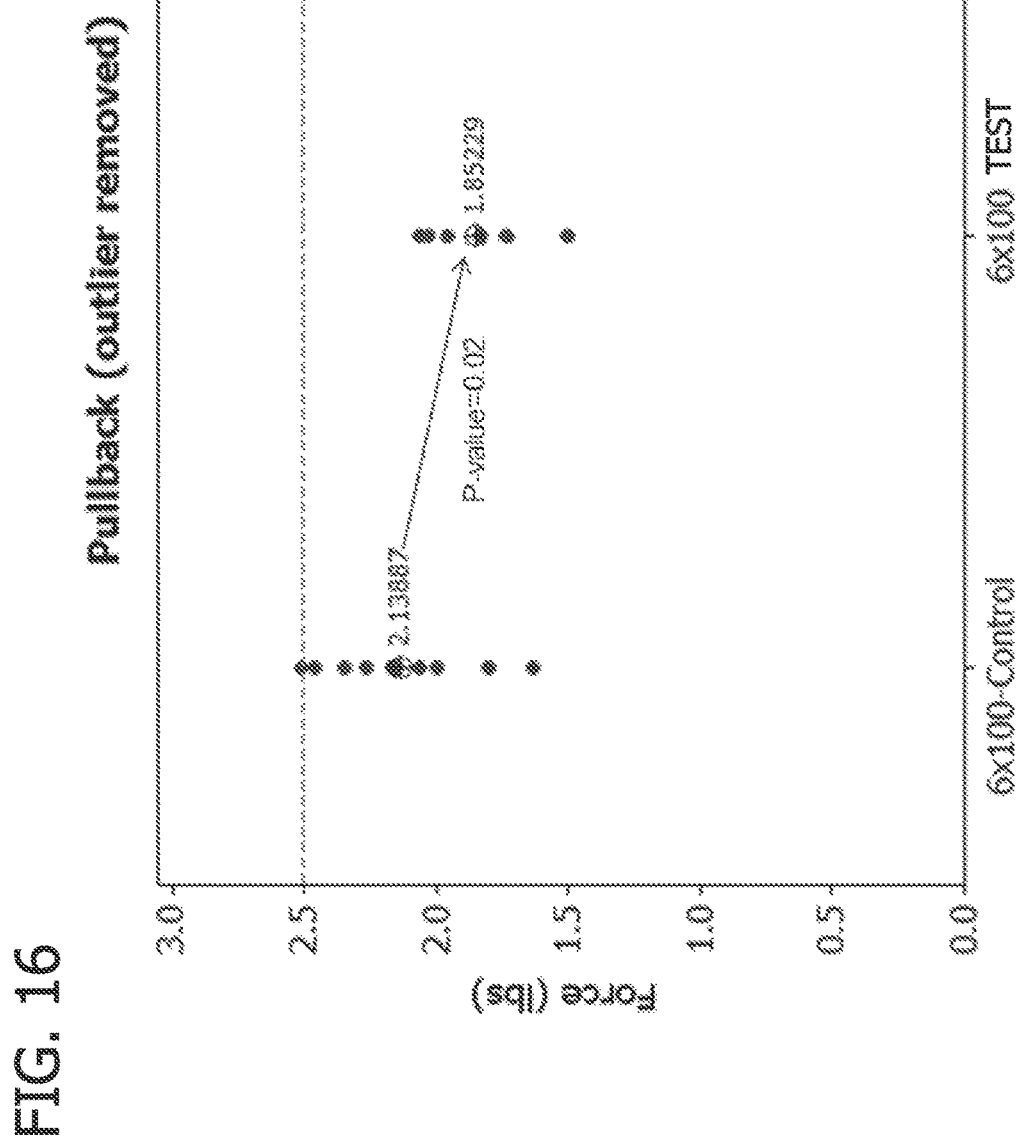
FIG. 16 is similar to FIG. 15, with data outliers removed therefrom.
Figure 17:
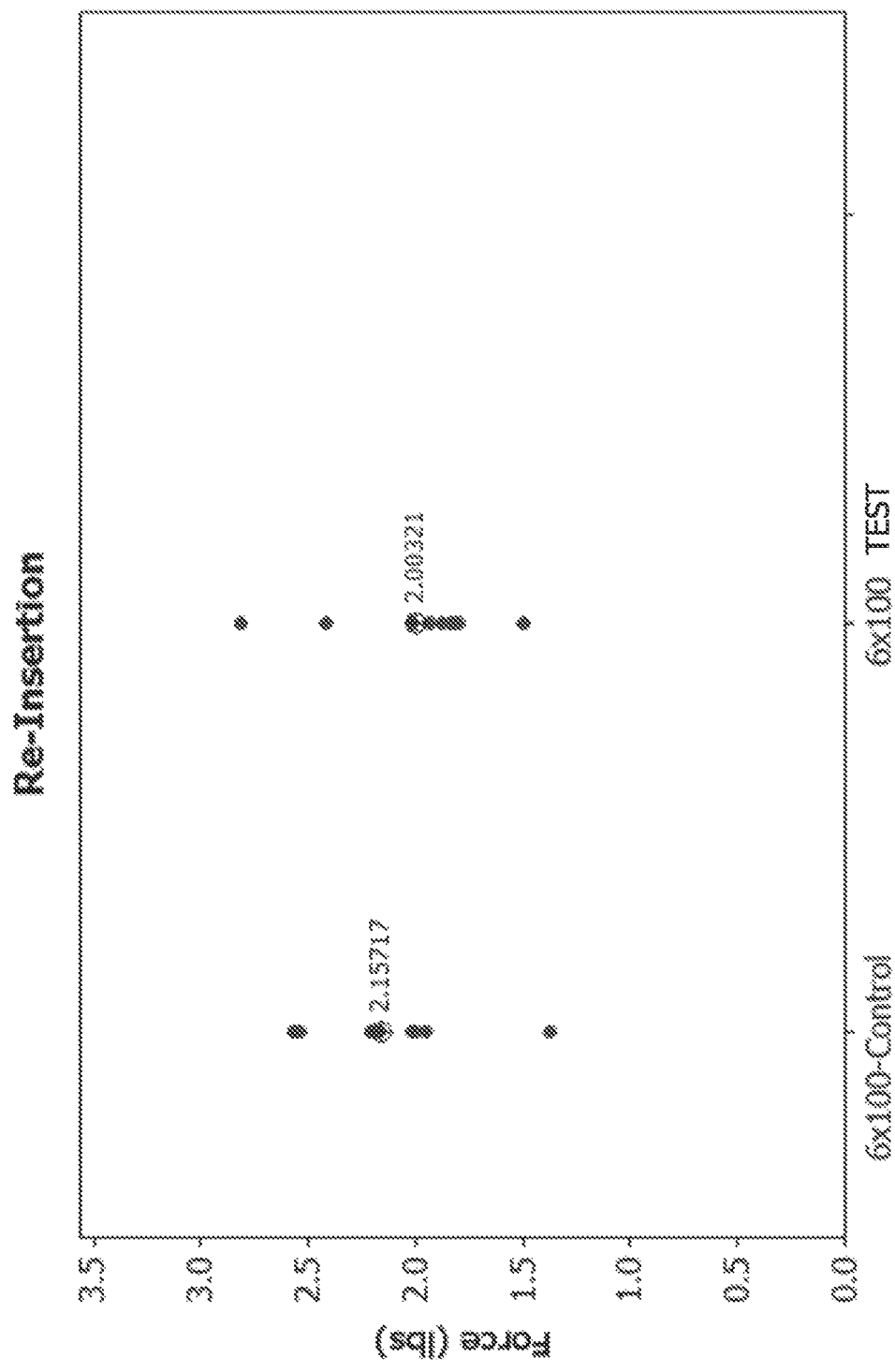
FIG. 17 is a chart depicting data collected during re-insertion force testing of test balloons and control balloons

As can be seen from FIGS. 15-17, both the pull-back force and the re-insertion force for the test balloon was significantly less than the control balloon, showing that the grooves 50 and/or the ribs 66 contributed to the reduced pull-back and re-insertion force. In one example, the pull-back force of the balloon may measure from about 1.93 lbs (8.59 N) to about 1.50 lbs (6.67 N).

Figure 18:
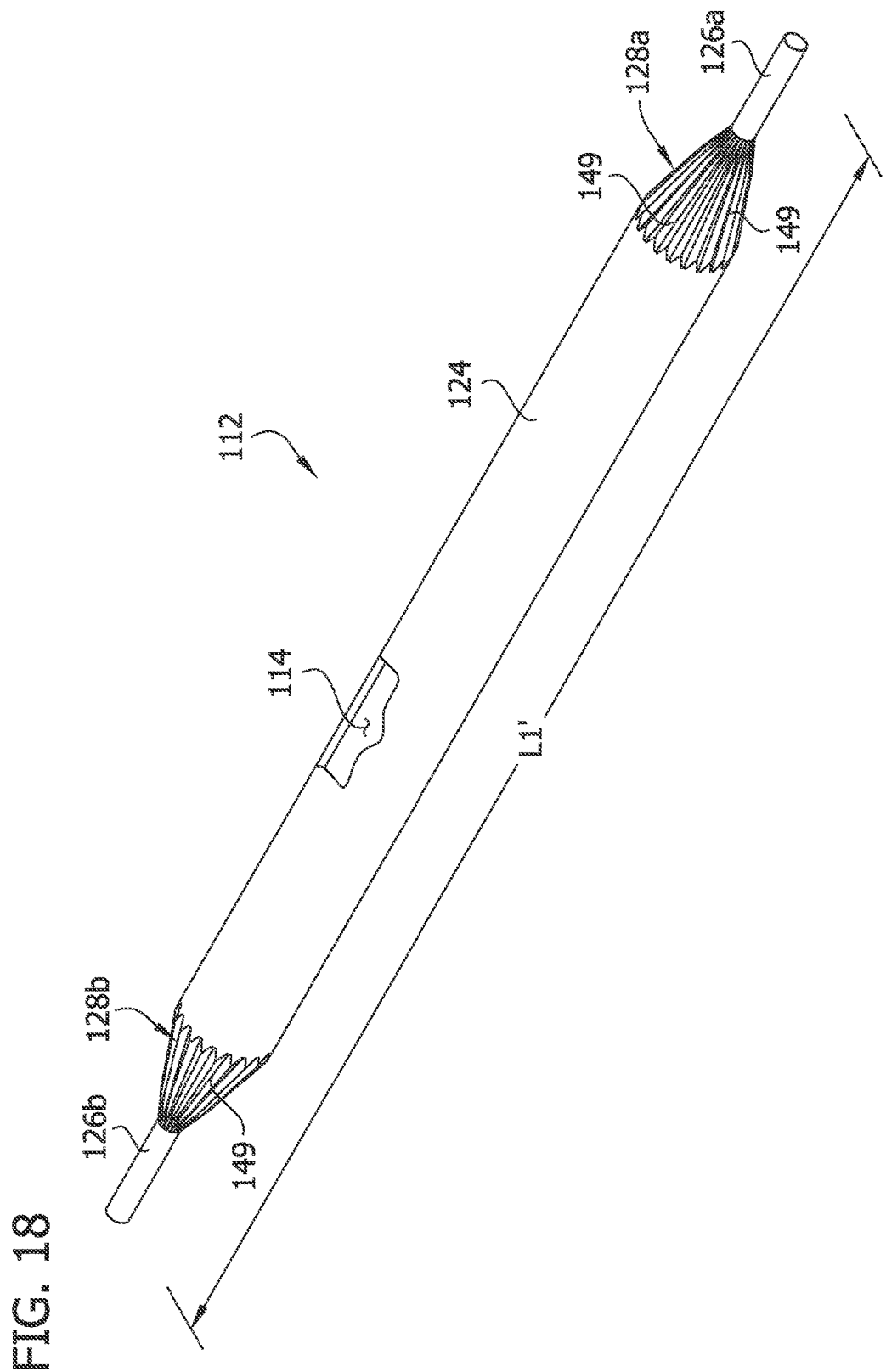
FIG. 18 is a perspective of another embodiment of a medical balloon for a balloon catheter.

Referring to FIG. 18, another embodiment of a medical balloon for a medical device is generally indicated at reference numeral 112 in FIG. 18. The medical balloon 112 has a length L1' and comprises a balloon body section 124; opposite distal and proximal waist sections 126a, 126b, respectively, at opposite longitudinal ends of the balloon; and opposite distal and proximal cone sections, generally indicated at 128a, 128b, respectively, at corresponding distal and proximal ends of the body section intermediate the body section and the corresponding distal and proximal waist sections. It is understood that the balloon 112 may have other sections, structures, and/or components without departing from the scope of the present invention. The balloon 112 may be formed from a polymer material, including, but not limited to, a thermoplastic polymer or a thermoplastic elastomer polymer.

Figure 19:
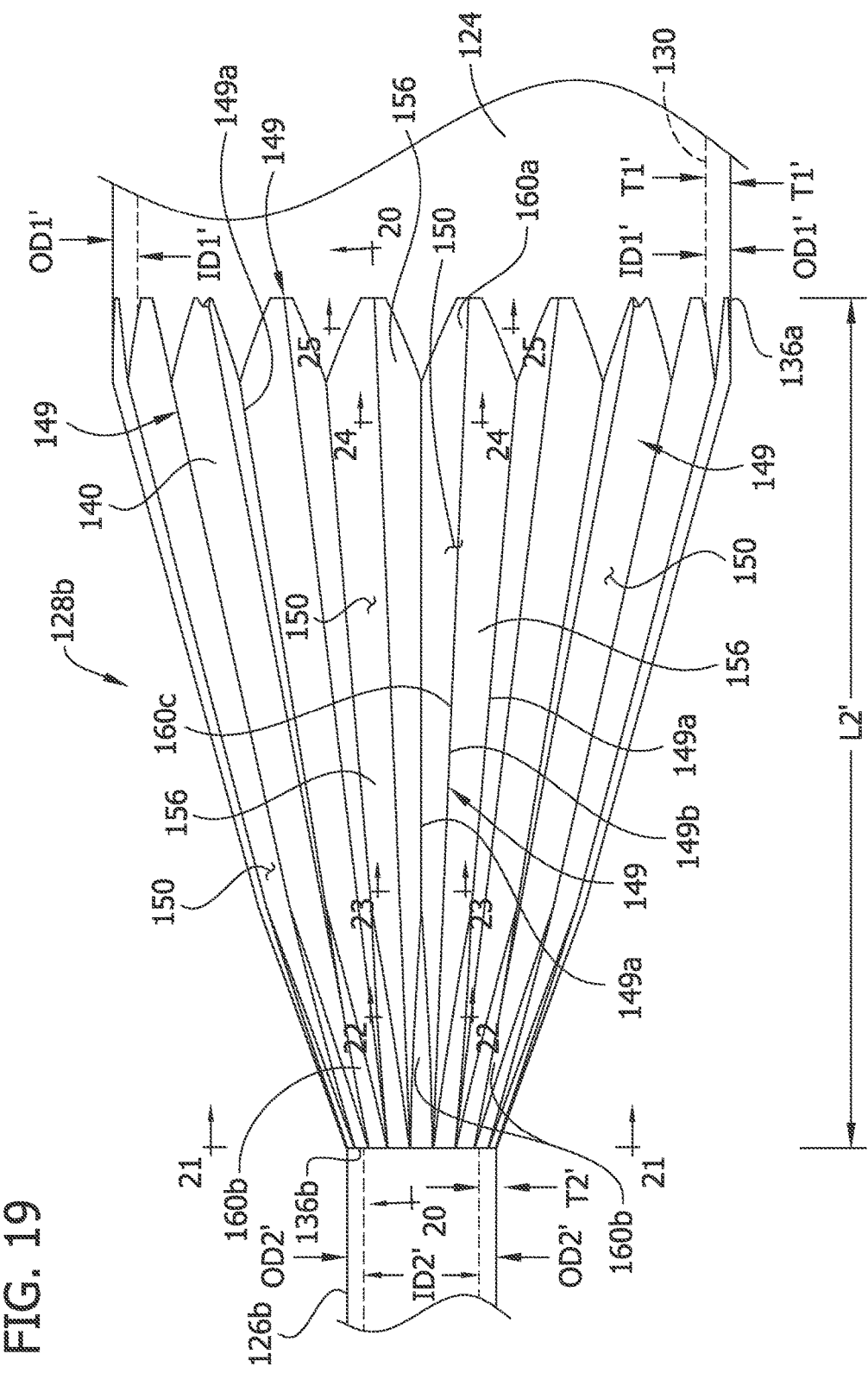
FIG. 19 is an enlarged, fragmentary side elevational view of the balloon of FIG. 18, showing a distal cone section, a portion of a distal waist section, and a portion of the body section thereof.

The body section 124 interconnects and is disposed between the distal and proximal cone sections 128a, 128b. In the illustrated embodiment, the body section 124 is generally tubular defining a portion of the interior chamber 114 for receiving fluid to expand an outer circumference (i.e., an outer dimension) of the body section. Referring to FIG. 19, the body section 124 has an expanded inner diameter ID1' (i.e., an inner cross-sectional dimension) defined by an interior surface 130 of the balloon 112, an expanded outer diameter OD1', and a thickness T1' that may be generally uniform along its length L1'. The body section 124 may have other shapes and dimensions without departing from the scope of the present invention.

The distal and proximal waist sections 126a, 126b are generally tubular and, in the illustrated embodiment, are configured to receive a catheter body (not shown) therein. Referring to FIG. 19, each waist section 126a, 126b has an outer diameter OD2' less than the outer diameter OD1' of the body section 124. Thicknesses T2' of the waist sections 126a, 126b may be greater than the thickness T1' of the body section 124. It is understood that the waist sections 126a, 126b may be omitted from the balloon 112 without departing from the scope of the present invention.

In general, the distal and proximal cone sections 128ab, 128b are mirror images of one another. For purposes of this disclosure, the proximal cone section 128b is shown in detail in the drawings, with the understanding that the teachings relating to the proximal cone section apply equally to the distal cone section 128a, with exceptions noted herein. Referring to FIG. 19, the proximal cone section 128b has distal and proximal ends 136a, 136b, a length L2' extending between the distal and proximal ends, and an exterior surface 140 having a generally conical (e.g., frustoconical) shape and a circumference or periphery (i.e., an outer dimension) and an outer diameter (i.e., an outer cross-sectional dimension) tapering proximally toward the proximal end of the proximal cone section. An interior surface 144 (FIG. 20) of the proximal cone section 128b also has a generally conical shape defining an inner circumference or periphery (i.e., an inner dimension) and an inner diameter (i.e., an inner cross-sectional dimension) of the cone section that taper proximally toward its proximal end 136b.

In the illustrated embodiment, the structures of the distal cone section 128a have inverse relationships with the corresponding structures of the proximal cone section 128b. Although not shown in detail in the drawings, the distal cone section 128a has distal and proximal ends, a length extending between the distal and proximal ends, and an exterior surface having a generally conical shape and defining an outer circumference or periphery (i.e., an outer dimension) and an outer diameter (i.e., an outer cross-sectional dimension) of the cone section that taper distally toward its distal end. An interior surface of the distal cone section also has a generally conical shape and defines an inner circumference or periphery (i.e., an inner dimension) and an inner diameter (i.e., an inner cross-sectional dimension) of the cone section that taper distally toward the distal end thereof.

Referring to FIG. 18, at least one of the cone sections 128a, 128b comprises pleats 149 to facilitate folding of the balloon 112. In the illustrated embodiment, each of the distal and proximal cone sections 128a, 128b defines such pleats 149, as shown in FIG. 18. In other embodiments, only the distal cone section 128a or only the proximal section 128b may include the pleats 149. Alternating inner and outer fold lines 149a, 149b are spaced circumferentially around the cone sections 128a, 128b. Referring to FIG. 19, outer fold lines 149a define outer most portions of the exterior surface 140 of the proximal cone section 128 and inner fold lines 149b define inner most portions of the exterior surface. The fold lines 149a, 149b extend along the length L2' of the proximal cone section 128b between the body section 124 and the proximal waist section 126b. Each pleat 149 includes adjacent side walls 156 joined at the corresponding inner fold line 149a; the side walls 156 extend away from one another to adjacent respective outer fold lines 149b. Exterior surfaces of the adjacent side walls 156 are in generally opposing relationship with respect to one another, while interior surfaces of the adjacent side walls face away from one another. The pleats 149 are juxtaposed (i.e. side-to-side) and define a plurality of side-by-side grooves 150 in the cone section 128a, 128b. As such the cone sections 128a, 128b shown in the illustrated embodiment generally have an accordion pleat configuration. However, other pleat configurations are envisioned.

Figure 21:
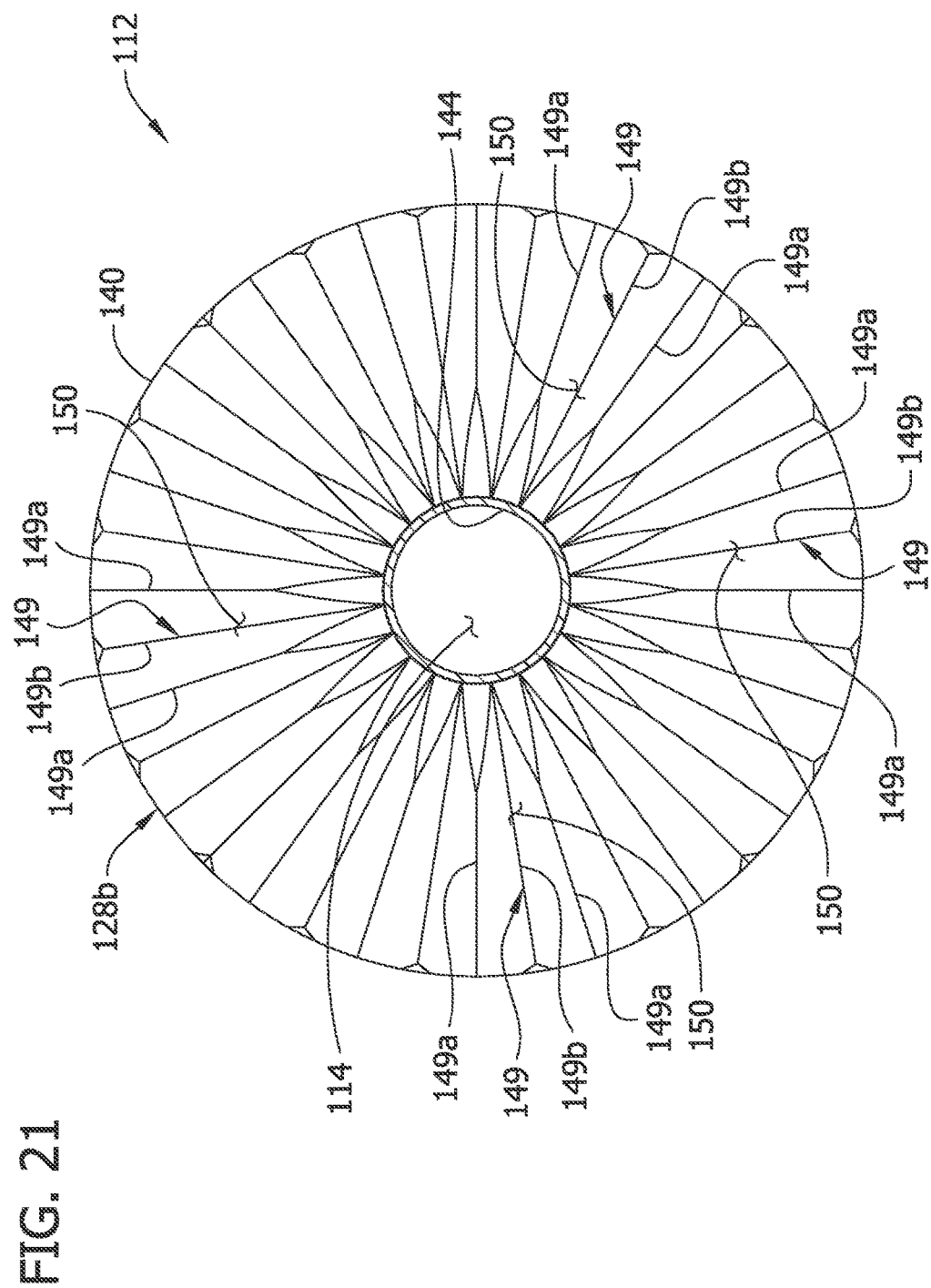
FIG. 21 is an enlarged section of the balloon taken along the line 21-21 in FIG. 19.

As seen in FIGS. 19 and 21, the grooves 150 are spaced around the outer circumference (i.e., outer periphery) of the corresponding cone section 128a, 128b, and in the illustrated embodiment, the grooves 150 are uniformly spaced around the outer circumference. Each groove 150 includes a central section 160c and opposite distal and proximal end sections

160a, 160b. One or both cone sections 128a, 128b may include any suitable number of grooves 150. In one example, the number of grooves 150 is based, at least in part, on the outer diameter OD1' (i.e., outer cross-sectional dimension) of the body portion 124 of the balloon 112 and the size and/or configuration of the pleats 149. For example, one or both of the cone sections 128a, 128b includes 2-3 grooves 150 for every millimeter in outer diameter OD1' of the body section 124. As an example, a balloon including a body section having an outer diameter measuring 8 mm will have about 20 grooves on one or both of the cone sections. In one embodiment, the pleats 149 are formed during blow molding, as explained below. In other embodiments, the pleats 149 may be formed in other ways, such as by grinding or laser ablation.

Figure 20:
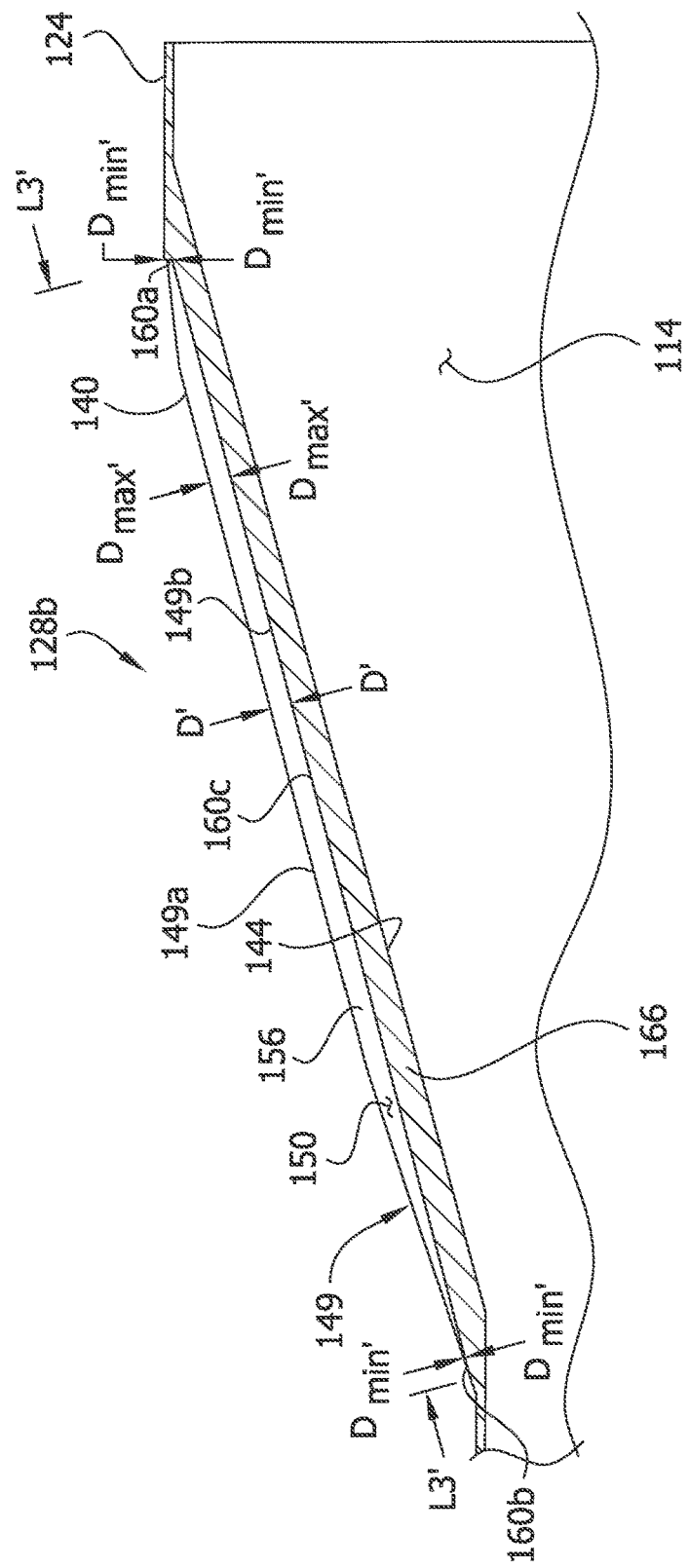
FIG. 20 is an enlarged, fragmentary section of the balloon taken along the line 20-20 in FIG. 19.

Referring to FIG. 20, a single groove 150 of the proximal cone section 128b is shown for illustrative purposes, with the understanding that the teachings of the illustrated groove apply equally to the other grooves of the cone section or sections. The groove 150 has a length L3' extending lengthwise of the proximal cone section 128b between the distal and proximal ends of the proximal cone section, and a depth D' extending inward from the exterior surface 140 of the proximal cone section. In the illustrated embodiment, the depth D' of at least a portion of the groove 150 tapers away from the central section 160c of the groove. That is, the depth D' of the groove 150 tapers proximally and distally away from the central section 160c. Similar, the depth of at least a portion of each groove 150 of the distal cone section 128a tapers proximally and distally away from the central section of each groove. Through this configuration, as shown in FIG. 20, a maximum depth $D_{max}'$ of each groove 150 is generally at the central section 160c of the groove 150. It is believed that the maximum depths $D_{max}'$ of the grooves 150 at these locations facilitate folding and refolding of the balloon 112 at the locations generally where the cone sections 128a, 128b have maximum thicknesses. Thus, the grooves 150 facilitate refolding of the balloon 112 after deflation to reduce the cross-sectional profile (e.g., the circumference) of the deflated balloon. Facilitating re-folding of the balloon 112 into a low cross-sectional profile decreases the pull-back force necessary to pull the balloon back into the introducer sheath after treatment. Through this configuration, also shown in FIG. 20, minimum depths $D_{min}'$ of each groove 150 are located at the distal and proximal end sections 160a, 160b of each groove. The minimum depths $D_{min}'$ at the distal and proximal end sections 160a, 160b produce smooth transitions between the proximal cone section 128b and the proximal waist section 126b at the proximal end section, and the proximal cone section and the body section 124 at the distal end section. The smooth transitions remove points of weakness that could be present with abrupt transitions. This can improve the overall strength of the balloon 112. It is understood that in other embodiments, the depths D' of the pleats may not taper lengthwise.

Figure 22:
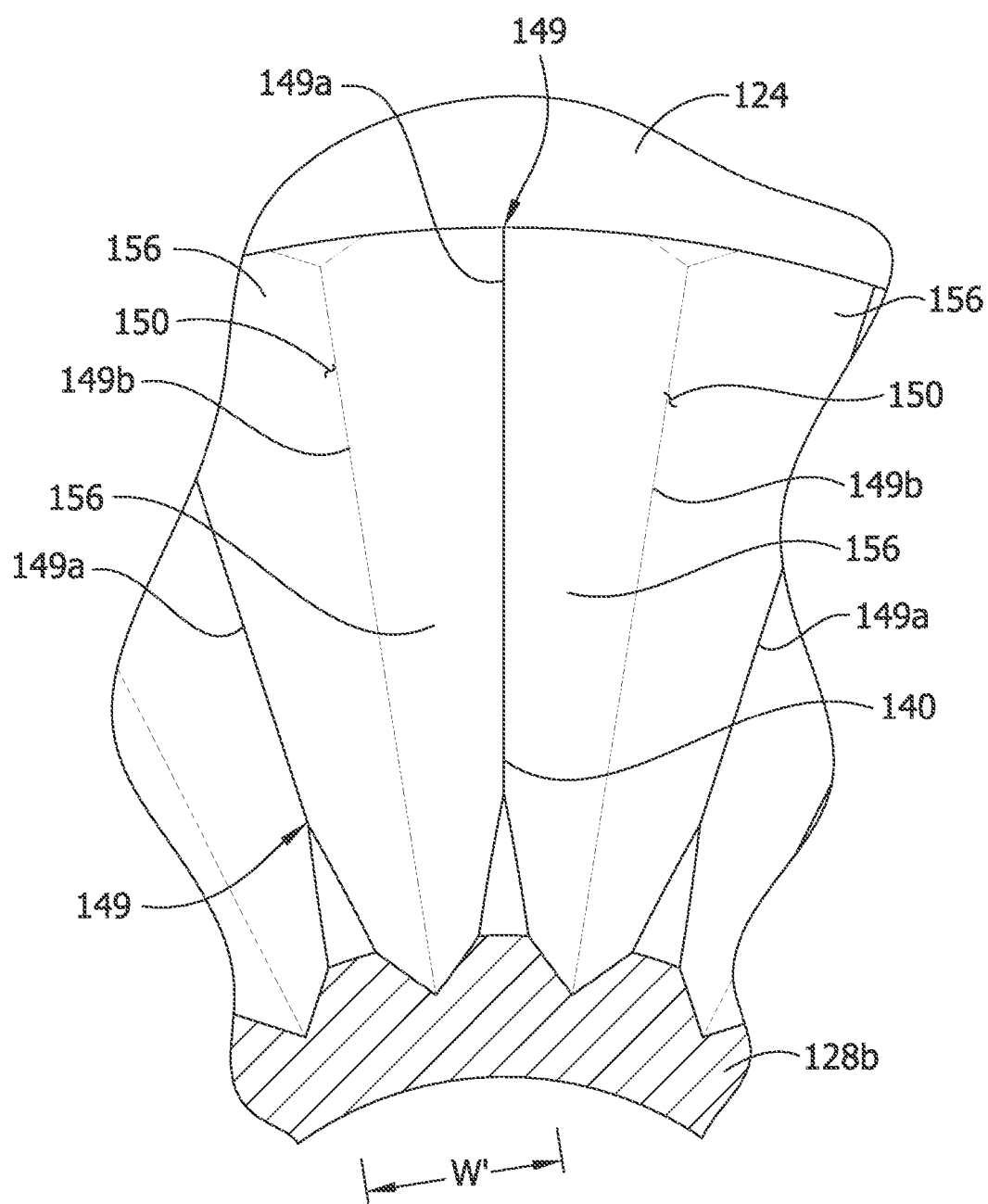
FIG. 22 is an enlarged, fragmentary section of the balloon taken along the line 22-22 in FIG. 19
Figure 23:
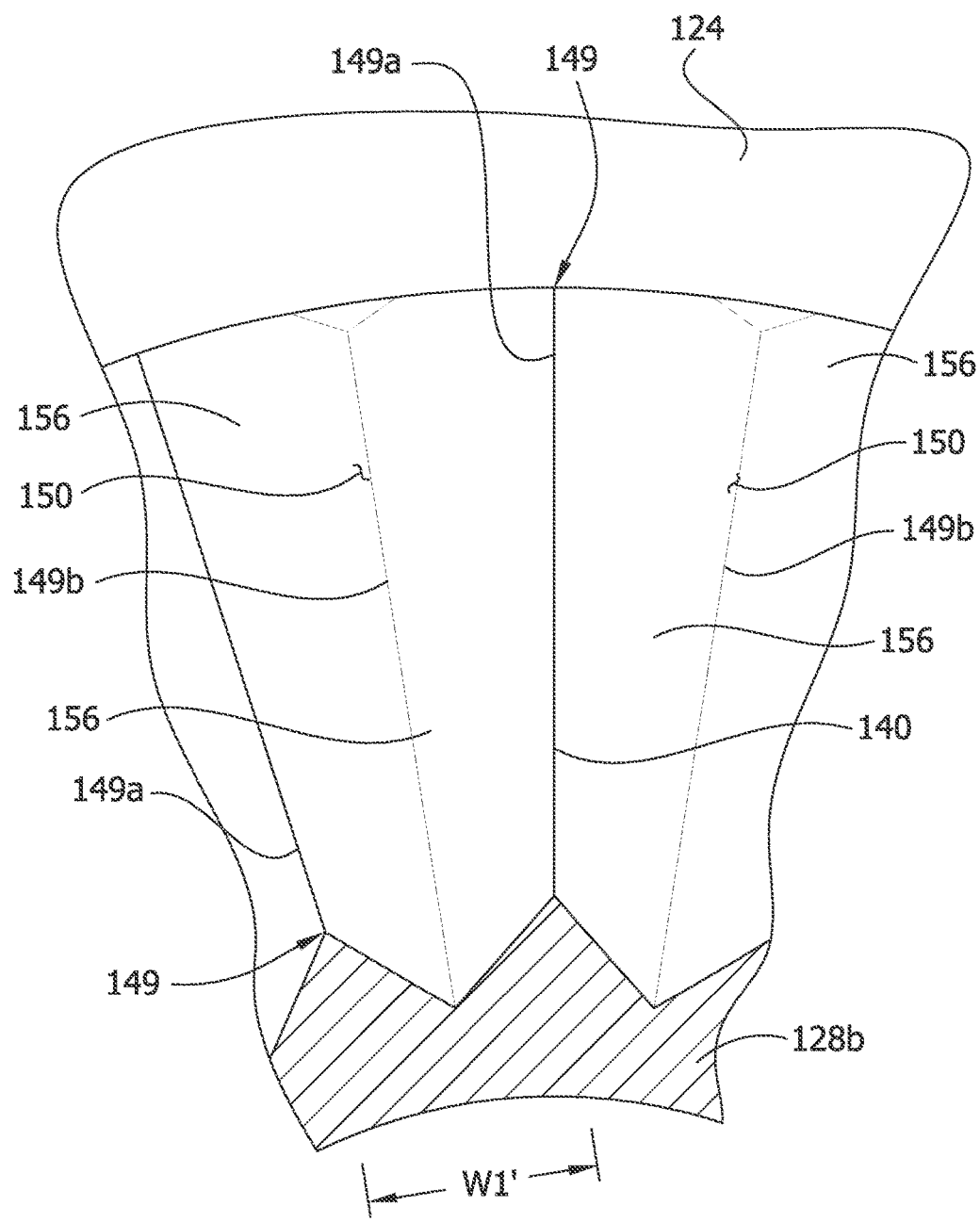
FIG. 23 is an enlarged, fragmentary section of the balloon taken along the line 23-23 in FIG. 19.
Figure 24:
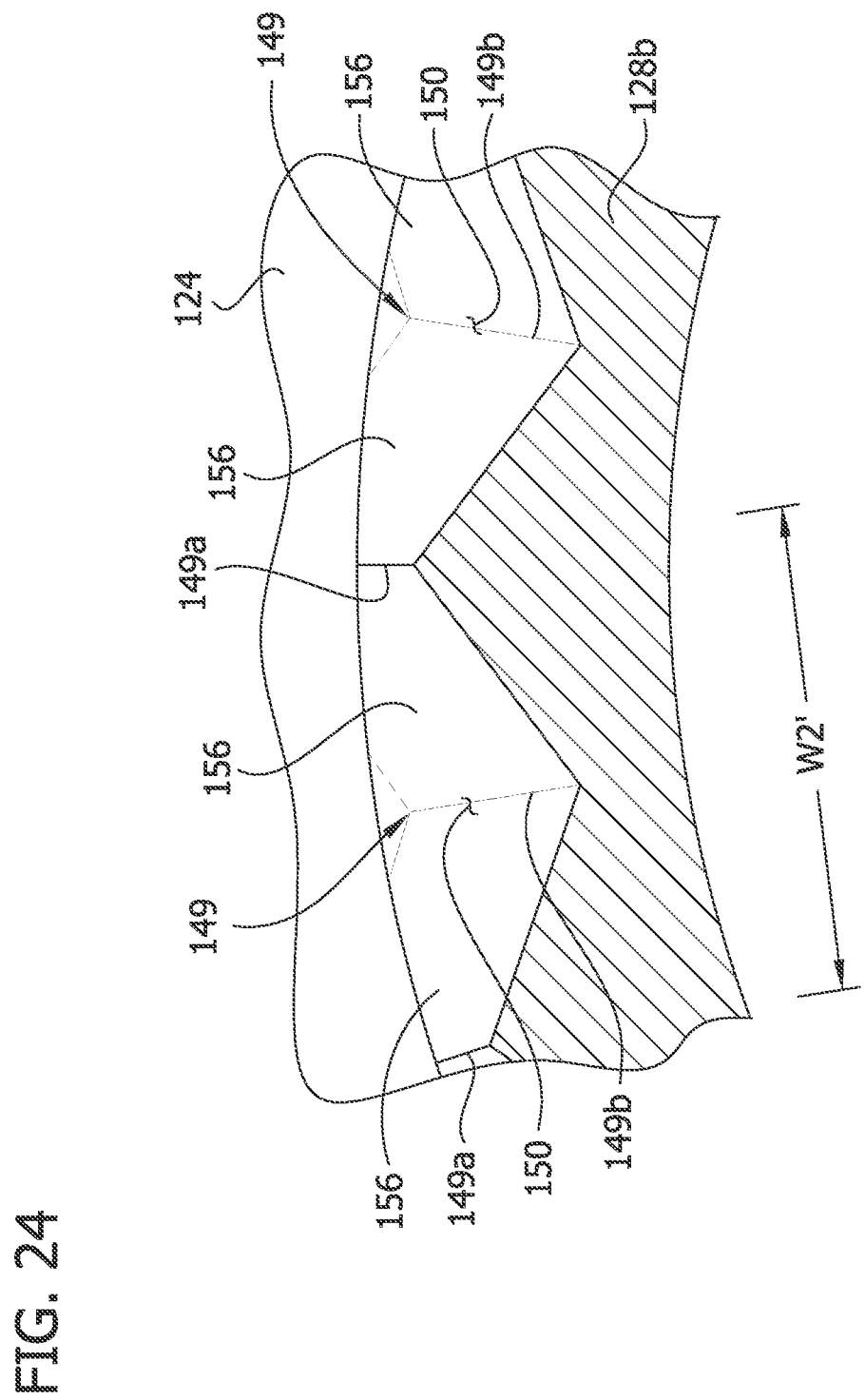
FIG. 24 is an enlarged, fragmentary section of the balloon taken along the line 24-24 in FIG. 19.
Figure 25:
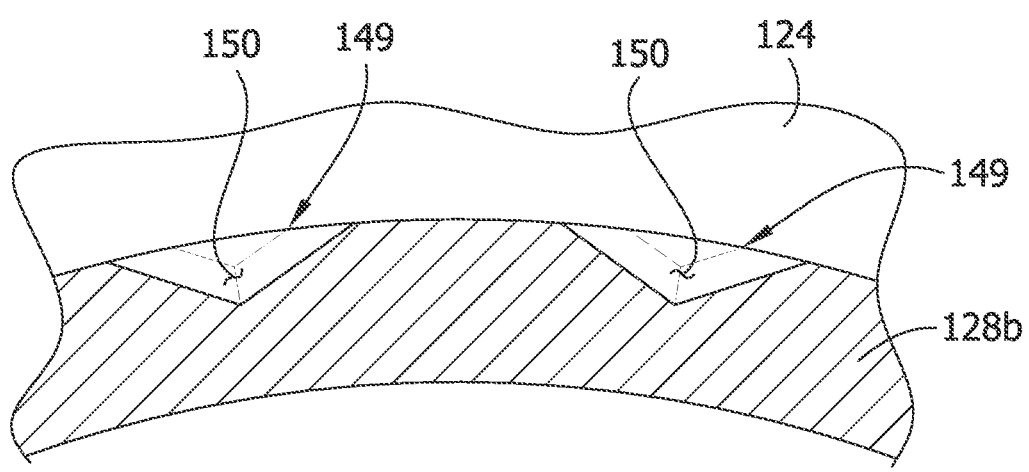
FIG. 25 is an enlarged, fragmentary section of the balloon taken along the line 25-25 in FIG. 19.

Referring to FIG. 22, the groove 150 has a width W' defined between adjacent outer folds 149a and extending circumferentially of the corresponding cone section. The width W' of at least a longitudinal portion of the groove 150 tapers away from the body section 124. That is, the width W' of at least a portion of each groove 150 of the proximal cone section 128b tapers proximally away from the distal end thereof and the body section 124, and the width of at least a portion of each groove of the distal cone section 128a tapers distally away from the proximal end thereof and the body section. This tapering width W' is also evident from FIGS. 23 and 24, where the width (indicated at W1') of the groove 150 taken at line 23-23 in FIG. 19 is less than the width (indicated at W2') of the groove taken at line 24-24 in FIG. 19. It is understood that in other embodiments, the widths W' of the grooves may not taper lengthwise or the widths may taper toward the body section.

As can be seen from FIGS. 22-26, in particular, the width W' of at least a portion of the groove 150 also tapers along the depth of the groove, i.e., from adjacent the outer folds 149a of the proximal cone section 128b toward the inner fold 149b of the groove. This configuration gives the groove 150 a triangular cross section and facilitates releasing of the blow-molded balloon from the mold. It is understood that in other embodiments, the widths W' of the grooves may not taper depthwise.

In the illustrated embodiment, the cone sections 128a, 128b have corresponding internal ridges or ribs 166 (FIG. 20) associated with the grooves 150 (e.g., each groove has an associated rib) and defined by the pleats 149. In other words, each of the proximal and distal cone sections 128a, 128b includes ribs 166 disposed at locations on the interior surface of the corresponding cone section generally corresponding to locations of the grooves 150 on the exterior surface of the corresponding cone section. The internal ribs 166 extend inward from the interior surface 144 of the corresponding cone section 128a, 128b. The dimensions of the ribs 166—including the lengths, widths, and radial distances' thereof—are based on the dimensions of mold ribs of the mold used to blow-mold the balloon and the thicknesses of the cone sections, which are based on the thickness of the parison and the dimensions (e.g., inner diameters) of the mold. In illustrated embodiment, the dimensions of each rib 166 are directly related to the dimensions of the corresponding groove 150. It is believed that the internal ribs 166 facilitate folding of the balloon 112. Thus, the ribs 166 facilitate refolding of the balloon 112 after deflation to reduce the cross-sectional profile (e.g., the circumference) of the deflated balloon. Facilitating re-folding of the balloon 112 into a low cross-sectional profile decreases the pull-back force necessary to pull the balloon back into the introducer sheath after treatment. In other embodiments, the cone sections may not include the internal ridges or ribs. As can be understood, in such an embodiment, the thicknesses of the cone sections are greater than the heights of the groove-forming ribs of the mold.

Figure 26:
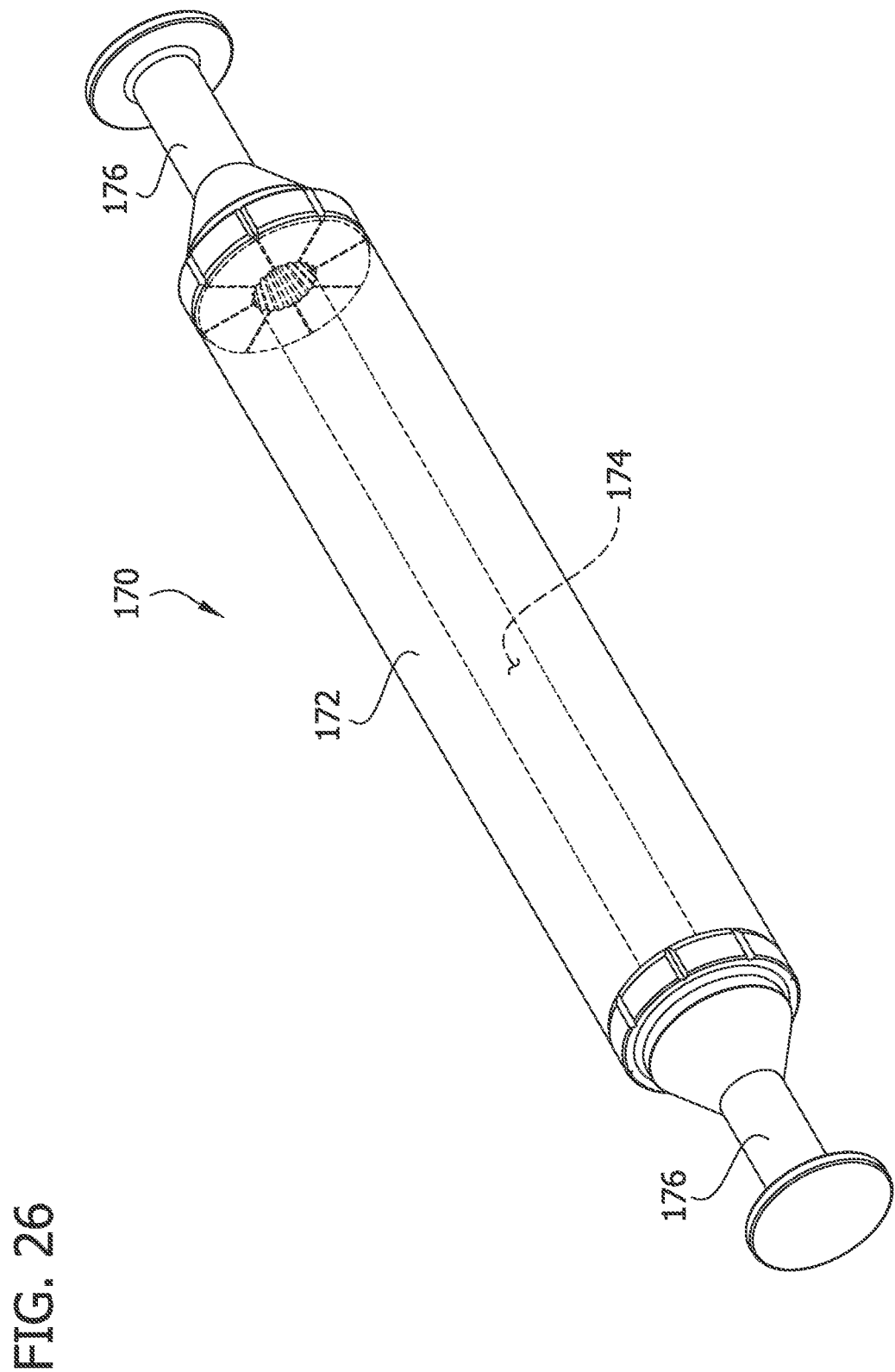
FIG. 26 is a schematic perspective of another embodiment of a blow mold for use in forming a balloon.
Figure 28:
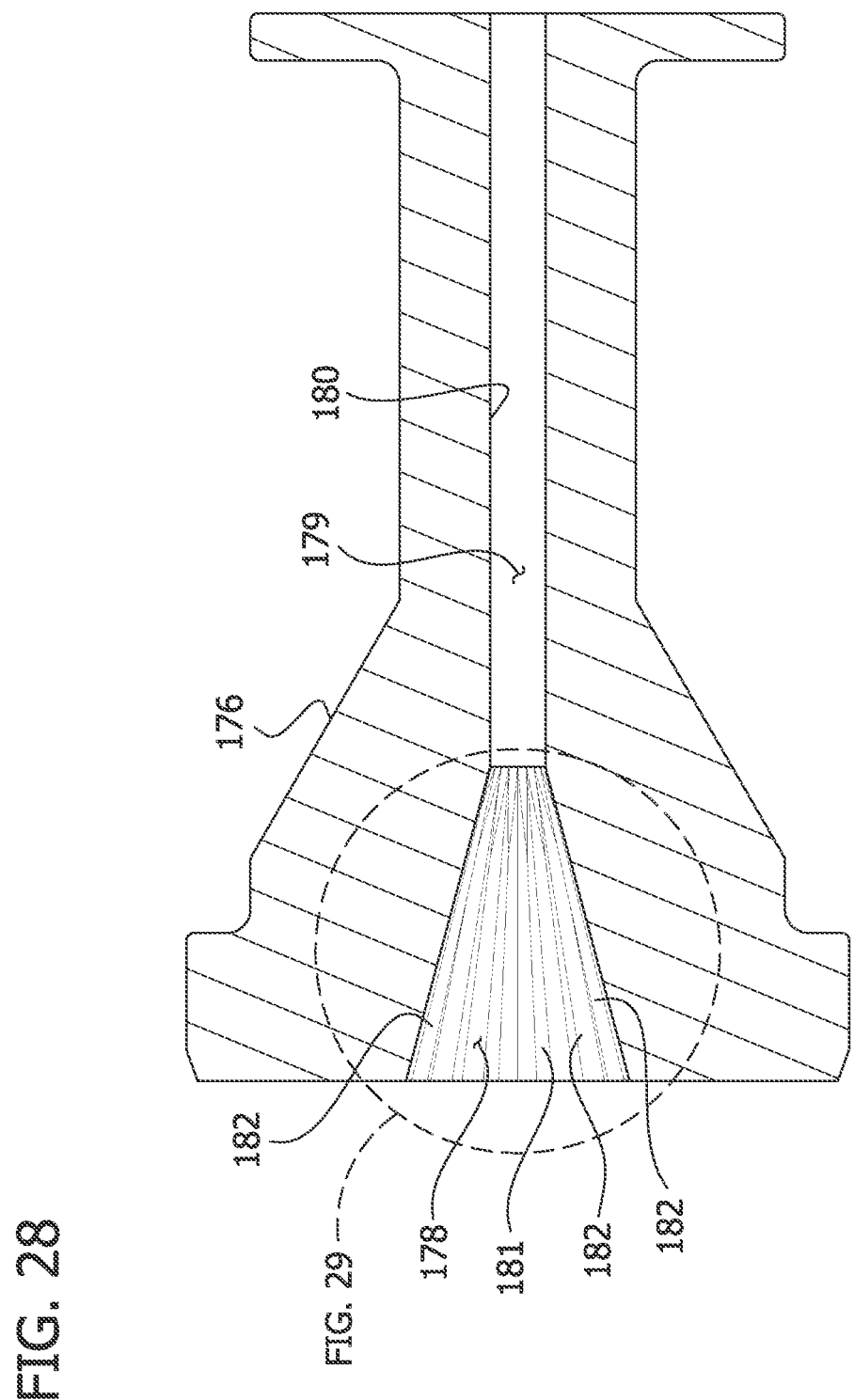
FIG. 28 is a longitudinal section of the cone-waist molding section in FIG. 27.

Referring to FIG. 26, an embodiment of a mold for use in blow molding the medical balloon 112 is illustrated schematically at reference numeral 170. The mold 170 comprises a body molding section 172 defining a body molding cavity 174, and opposite proximal and distal cone-waist molding sections, generally indicated at 176, at respective proximal and distal ends of the body molding section and defining respective cone molding cavities 178 and waist molding cavities 179 (FIG. 28). The body molding cavity 174 is generally cylindrical having a circumference that defines an outer circumference (i.e., an outer dimension) of the body section 124 of the blow molded balloon 112. The cone molding cavity 178 of the cone-waist molding section 176 is used to form the corresponding distal and proximal balloon cones 128a, 128b during blow molding, and the waist molding cavities 176 are used to form the corresponding distal and proximal balloon waists 126a, 126b during blow molding.

Figure 27:
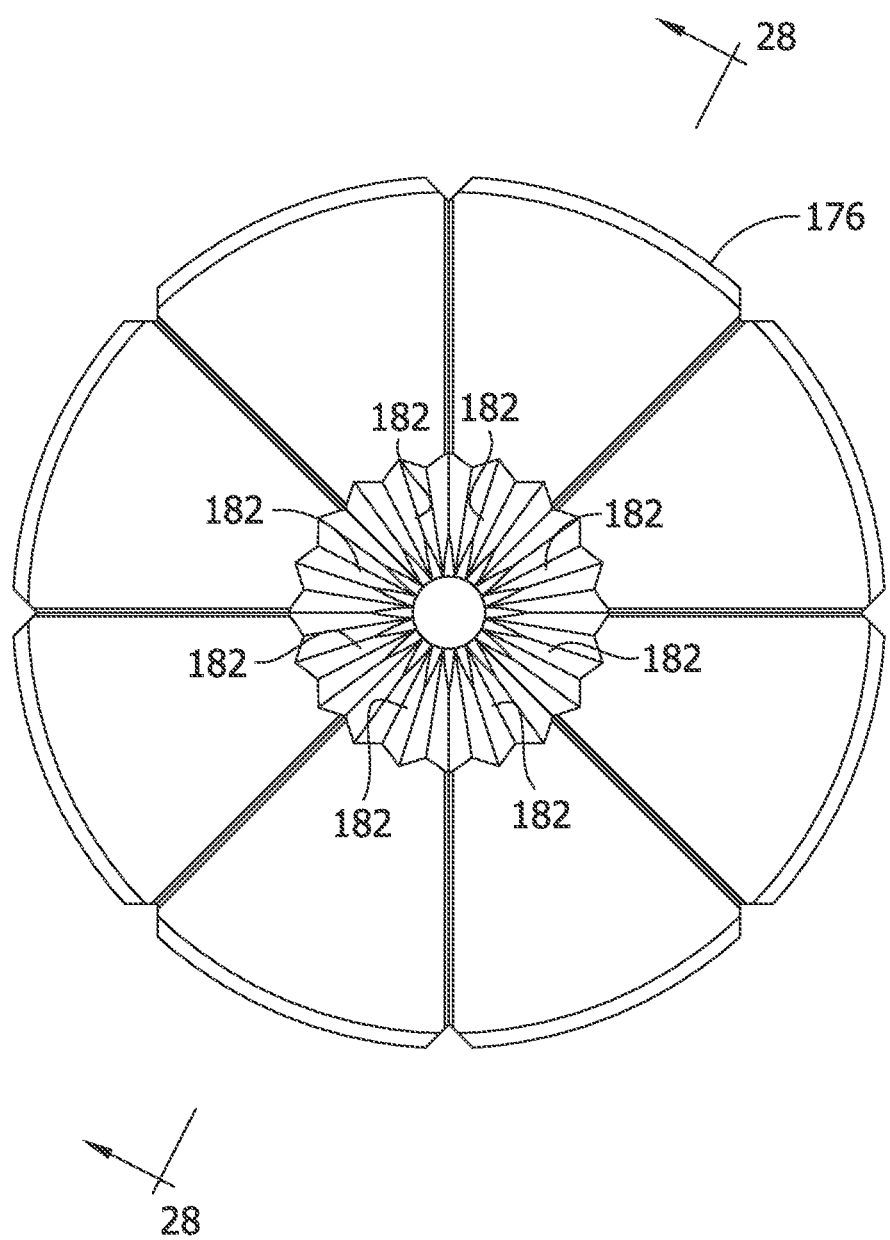
FIG. 27 is a front elevational view of a cone-waist molding section of the blow mold in FIG. 26.
Figure 29:
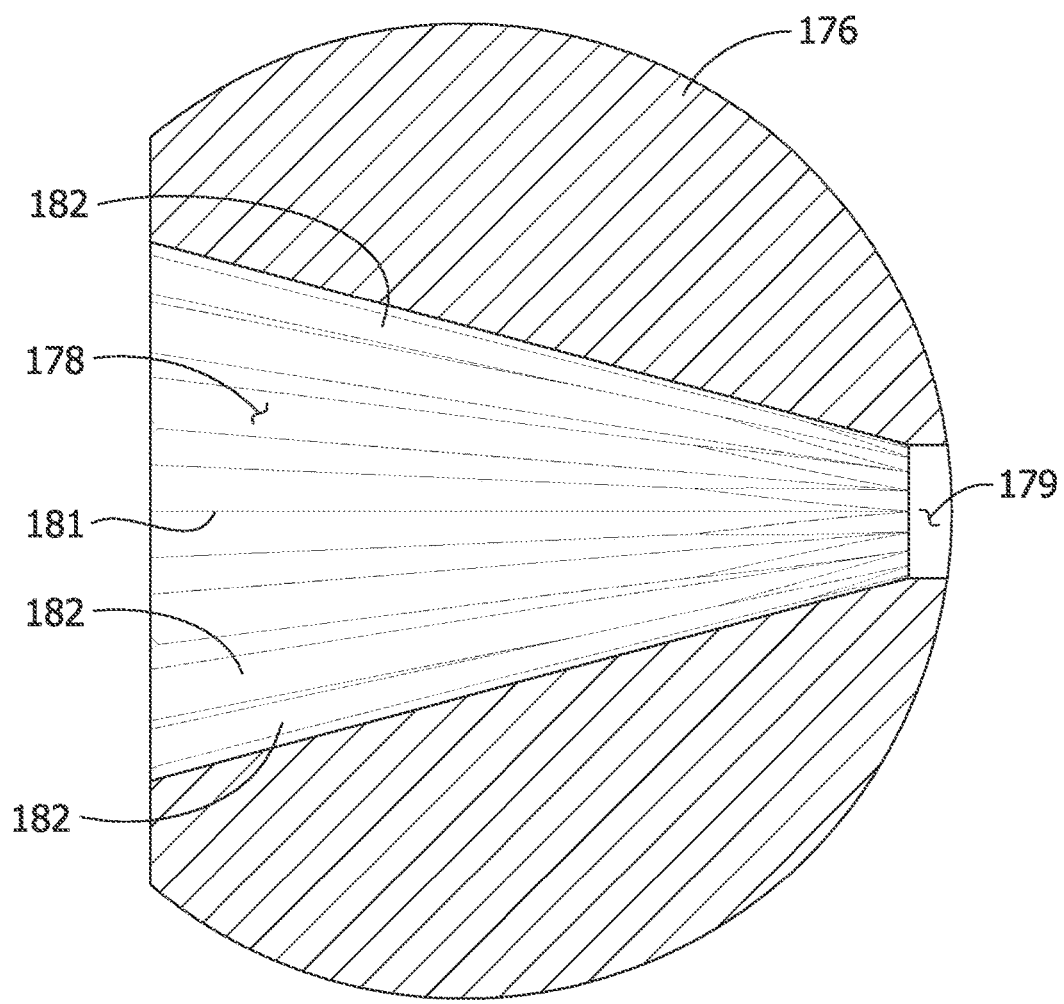
FIG. 29 is an enlarged, partial view of FIG. 28.

Referring to FIGS. 27-29, one of the cone-waist molding sections 176 will be described with the understanding that the other cone-waist molding section is identical, other than being positioned on an opposite end of the body molding section 172. The waist molding cavity 179 is defined by a generally cylindrical shaped interior surface 180 of the cone-waist molding section 176, although the interior surfaces defining the waist molding cavities may have shapes other than cylindrical without departing from the scope of the present invention. The cone molding cavity 178 is defined by a generally conical shaped interior surface 181 of the corresponding cone-waist molding section 176, and a plurality of molding ribs 182 extending radially inward from the interior surface. As can be understood, the shape and sizes of the respective interior surface 181 and molding ribs 182 of the illustrated cone-waist molding section 176 are suitable for forming the cone sections 128a, 128b of the illustrated balloon 112 during a blow molding process. For example, the conical interior surface 181 of the cone-waist molding section 176 has a size and shape corresponding to the size and shape of the exterior surfaces 140 of the cone sections 128a, 128b of the balloon 112. Moreover, the molding ribs 182 have sizes, shapes and locations corresponding to the sizes, shapes and locations of the grooves 150 of the cone sections 128a, 128b of the balloon.

Figure 30:
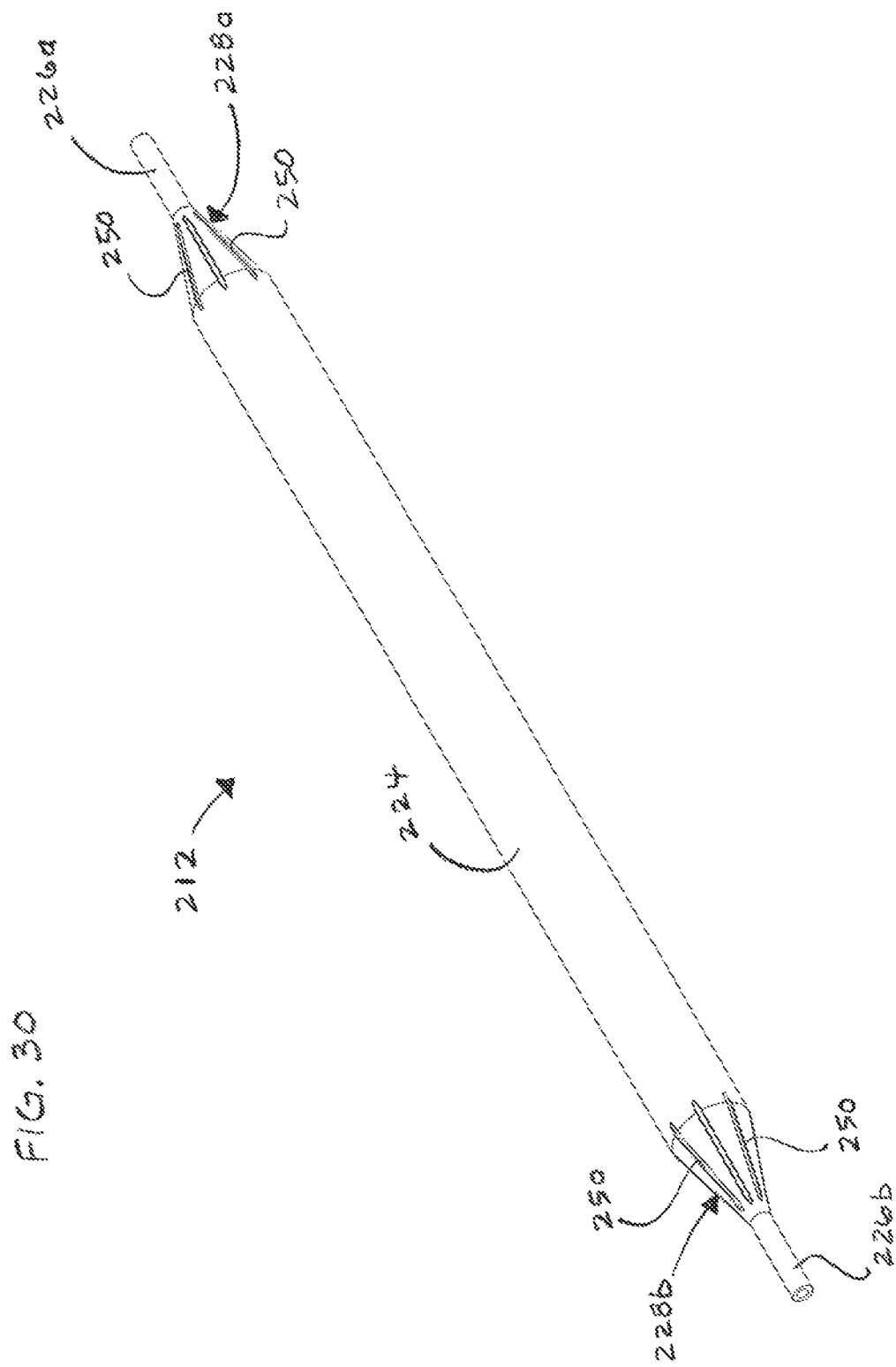
FIG. 30 is a perspective of another embodiment of a medical balloon for a balloon catheter, similar to the first embodiment.
Figure 31:
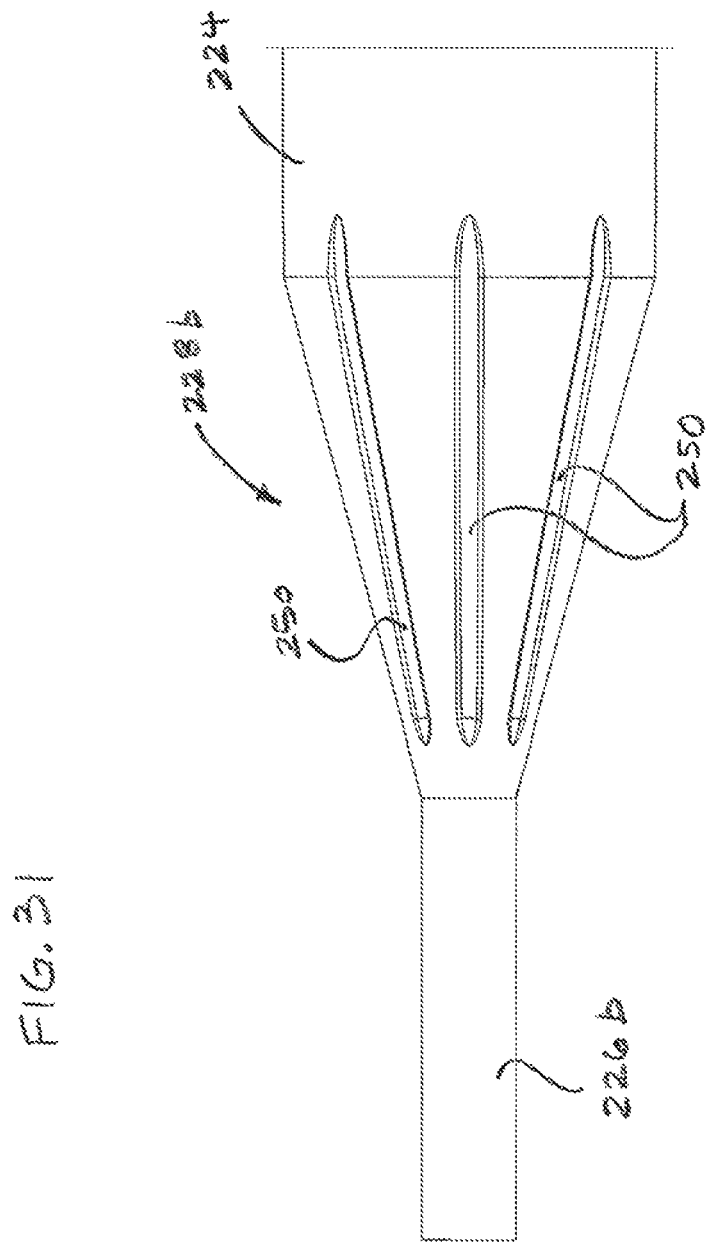
FIG. 31 is an enlarged, fragmentary side elevational view of the balloon of FIG. 30, showing a distal cone section, a portion of a distal waist section, and a portion of the body section thereof.

Referring to FIGS. 30 and 31, another embodiment of a medical balloon for a balloon catheter is generally indicated at reference numeral 212. Unless otherwise specifically indicated below, the medical balloon is substantially similar to the first medical balloon 12 described above. Like the first medical balloon 12, the medical balloon 212 has a length and comprises a balloon body section 224; opposite proximal and distal waist sections 226a, 226b, respectively, at opposite longitudinal ends of the balloon; and opposite proximal and distal cone sections, generally indicated at 228a, 228b, respectively, at corresponding proximal and distal ends of the body section intermediate the body section and the corresponding proximal and distal waist sections. Also like the first balloon 12, the body section 224, waist sections 226a, 226b, and cone sections 228a, 228b of the present balloon 212 may be integrally formed during a blow molding process to form the balloon as a one-piece construction. It is understood that the balloon 212 may have other sections, structures, and/or components without departing from the scope of the present invention.

As shown best in FIG. 31, the main difference between this medical balloon 212 and the first medical balloon 12 is that grooves 250 of the present balloon—which may be similar or identical in shape, size and/or number as the grooves 50—extend from the respective proximal and distal cone sections 228a, 228b to the body section 224. In particular, each groove 250 is a continuous groove, such that one longitudinal end of the groove is located in the corresponding cone section 228a, 228b, and the other longitudinal end of the groove is located in the body section 224. In another embodiment, respective grooves formed in the body section 224 (not shown) may connect with the longitudinal ends of the corresponding grooves 250 located in the body section.

Figure 32:
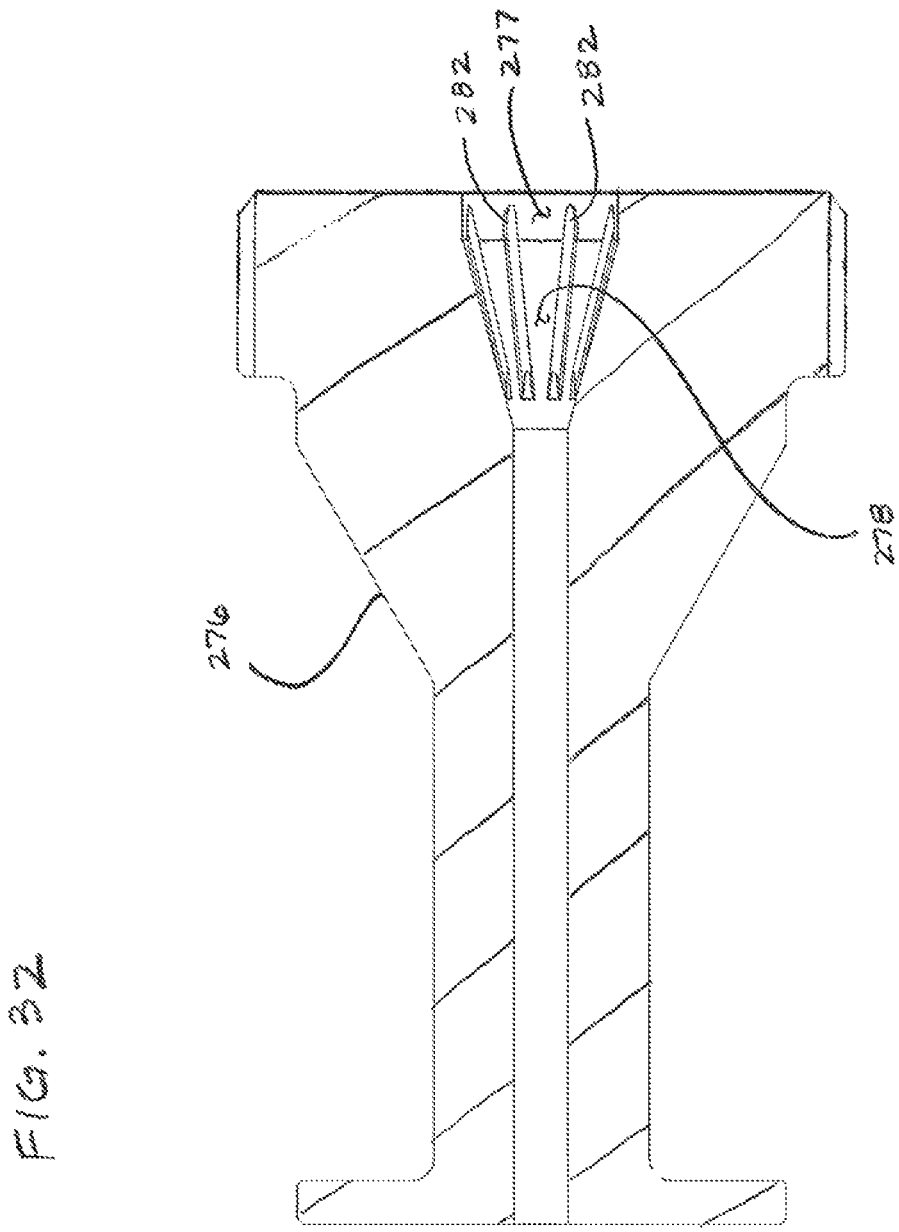
FIG. 32 is longitudinal section of a cone-waist molding section for forming a portion of the medical balloon.

Referring to FIG. 32, a suitable one of cone-waist molding sections 276 for forming the balloon 212 in a manner similar to that described above with respect to the balloon 12 will be described with the understanding that the other cone-waist molding section is identical, other than being positioned on an opposite end of a body molding section (not shown). Unless otherwise specifically indicated below, the cone-waist molding section 276 may be substantially similar to the first cone-waist molding section 76. The main difference between present cone-waist molding section 276 and the first cone-waist molding section 76 is that the present cone-waist molding section includes a partial body molding cavity 277 for molding a portion of the body section 224 that includes corresponding longitudinal end portions of the grooves 250. A plurality of molding ribs 282 extend from a waist molding cavity 278 to the partial body molding cavity 277 for forming the waist section 226b, the cone section 228b, the aforementioned portion of the body section 224, and the grooves 250. It is understood that the balloon 212 may be formed in other ways without departing from the scope of the present invention.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A balloon for a balloon catheter comprising:
a proximal cone section having proximal and distal ends, a length extending between the proximal and distal ends, an exterior surface having a generally conical shape, an interior surface, a wall thickness between the exterior and interior surfaces, and a circumference tapering proximally toward the proximal end of the proximal cone section;
a distal cone section having proximal and distal ends, a length extending between the proximal and distal ends, an exterior surface having a generally conical shape, an interior surface, a wall thickness between the exterior and interior surfaces, and a circumference tapering distally toward the distal end of the distal cone section; and
a balloon body section extending between and interconnecting the distal end of the proximal cone section and the proximal end of the distal cone section, the proximal and distal cone sections and the balloon body section defining an interior chamber configured to receive fluid to expand the balloon from a non-expanded state to an expanded state,
wherein one of the proximal and distal cone sections comprises grooves spaced apart around the circumference of said one of the proximal and distal cone sections, each groove having a length extending lengthwise of said one of the proximal and distal cone sections, a depth extending inward from the exterior surface of said one of the proximal and distal cone sections, and a width extending circumferentially of said one of the proximal and distal cone sections,
wherein the width of at least a portion of each groove tapers toward the balloon body section, and
wherein said one of the proximal and distal cone sections includes a plurality of ribs extending inward from the interior surface of said one of the proximal and distal cone sections at locations of the grooves on the exterior surface of said one of the proximal and distal cone sections such that each of the plurality of ribs extends at the respective location of each groove.

2. The balloon set forth in claim 1, wherein the depth of at least a portion of each groove tapers toward the balloon body section.

3. The balloon set forth in claim 2, wherein each groove is defined by a bottom portion, opposing side wall portions extending from respective sides of the bottom portion to the exterior surface of said one of the proximal and distal cone sections, wherein the bottom portion has a central longitudinal section and opposite distal and proximal end sections extending from corresponding distal and proximal ends of the central longitudinal portion to the exterior surface of said one of the proximal and distal cone sections.

4. The balloon set forth in claim 3, wherein the distal and proximal end sections of the bottom portion are generally flat and extend at angles offset from a circumferential plane defined by the circumference of said one of the proximal and distal cone sections.

5. The balloon set forth in claim 3, wherein the central longitudinal portion of the bottom portion of each groove is generally arcuate in cross section.

6. The balloon set forth in claim 3, wherein the width of at least a portion of each groove tapers from adjacent the exterior surface of said one of the proximal and distal cone sections toward the bottom portion of the groove.

7. The balloon set forth in claim 1, wherein each groove is partially defined by a bottom portion spaced apart from the exterior surface of said one of the proximal and distal cone sections, wherein the width of at least a portion of each groove tapers from adjacent the exterior surface of said one of the proximal and distal cone sections toward the bottom portion of the groove.

8. The balloon set forth in claim 7, wherein the depth of at least a portion of each groove tapers toward the balloon body section.

9. The balloon set forth in claim 1, wherein the balloon has a pull-back force from about 1.93 lbs (8.59 N) to about 1.50 lbs (6.67 N).

10. The balloon set forth in claim 1, in combination with a catheter, wherein the balloon is secured to the catheter.

11. The balloon set forth in claim 1, wherein said one of the proximal and distal cone sections is the proximal cone section.

12. The balloon set forth in claim 11, wherein the distal cone section comprises additional grooves spaced apart around the circumference of the distal cone section, each additional groove having a length extending lengthwise of the distal cone section, a depth extending inward from the exterior surface of the distal cone section, and a width extending circumferentially of the-distal cone section, wherein the width of the additional groove tapers toward the balloon body section.

* * * * *